(12) United States Patent
Fredrick

(10) Patent No.: US 7,517,498 B2
(45) Date of Patent: Apr. 14, 2009

(54) APPARATUS FOR SUBSTRATE HANDLING

(75) Inventor: Joseph P. Fredrick, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 867 days.

(21) Appl. No.: 10/643,424

(22) Filed: Aug. 19, 2003

(65) Prior Publication Data

US 2005/0042768 A1    Feb. 24, 2005

(51) Int. Cl.
    B01L 3/00    (2006.01)
(52) U.S. Cl. .................. 422/101; 422/102; 422/103; 422/58; 422/68.1; 436/174; 436/177; 436/180
(58) Field of Classification Search ........... 422/99–104, 422/58–68.1; 436/174, 180, 177
    See application file for complete search history.

(56) References Cited

U.S. PATENT DOCUMENTS

| 4,406,170 A | * | 9/1983 | Kuhn | |
| 4,738,824 A | * | 4/1988 | Takeuchi | ..................... 422/63 |
| 4,801,431 A | * | 1/1989 | Cuomo et al. | |
| 4,847,208 A | * | 7/1989 | Bogen | |
| 5,023,187 A | * | 6/1991 | Koebler et al. | |
| 5,073,504 A | * | 12/1991 | Bogen | |
| 5,100,626 A | * | 3/1992 | Levin | |
| 5,192,503 A | * | 3/1993 | McGrath et al. | .............. 422/57 |
| 5,278,048 A | * | 1/1994 | Parce et al. | |
| 5,527,510 A | * | 6/1996 | Atwood et al. | |
| 5,595,707 A | | 1/1997 | Copeland et al. | |
| 5,645,114 A | | 7/1997 | Bogen et al. | |
| 5,947,167 A | | 9/1999 | Bogen et al. | |
| 5,958,341 A | * | 9/1999 | Chu | |
| 5,958,760 A | | 9/1999 | Freeman | |
| 6,093,574 A | | 7/2000 | Druyor-Sanchez et al. | |
| 6,180,061 B1 | | 1/2001 | Bogen et al. | |

(Continued)

FOREIGN PATENT DOCUMENTS

| WO | WO 01/31347 | 5/2001 |
| WO | WO 01/32934 | 5/2001 |

OTHER PUBLICATIONS

Tecan HS 4800 Hybridization Station Specifications, Tecan USA http://www.tecan.com.

(Continued)

Primary Examiner—Brian R. Gordon

(57) ABSTRACT

Devices, apparatus and methods are disclosed for carrying out processing steps involved in chemical reactions such as hybridization reactions conducted on the surface of a substrate comprising chemical compounds such as biopolymer features. A device comprises a housing comprising a housing chamber. The housing comprises an opening through which a substrate may be inserted into the housing chamber. The device may also comprise a lift mechanism for moving the substrate in and out of the housing chamber in a controlled manner. At least one inlet may be in fluid communication with the housing chamber and at least one outlet may be in fluid communication with the housing chamber. Also disclosed are methods wherein the surface is brought into contact with a processing fluid; and, then, the surface is removed from contact with the fluid in a controlled manner at a rate that substantially eliminates droplet formation of the fluid on the surface of the substrate.

15 Claims, 6 Drawing Sheets

U.S. PATENT DOCUMENTS

| | | | |
|---|---|---|---|
| 6,183,693 | B1 | 2/2001 | Bogen et al. |
| 6,261,523 | B1 | 7/2001 | Schembri |
| 6,448,066 | B1 * | 9/2002 | Wheatcroft |
| 6,489,171 | B1 * | 12/2002 | Aghassi et al. |
| 6,673,620 | B1 * | 1/2004 | Loeffler et al. |
| 6,703,247 | B1 | 3/2004 | Chu |
| 6,759,011 | B1 * | 7/2004 | Richards et al. |
| 6,821,072 | B2 * | 11/2004 | Thiem et al. |
| 6,911,343 | B2 * | 6/2005 | Schembri et al. |
| 6,939,032 | B2 * | 9/2005 | Cosby et al. |
| 7,015,041 | B2 * | 3/2006 | Santarsiero et al. ............ 436/4 |
| 7,025,935 | B2 * | 4/2006 | Jones et al. ................. 422/100 |
| 7,153,474 | B2 * | 12/2006 | Thiem |
| 7,214,348 | B2 * | 5/2007 | Desmond et al. |
| 2002/0142470 | A1 * | 10/2002 | Clarke et al. |
| 2002/0164820 | A1 * | 11/2002 | Brown |
| 2003/0099580 | A1 * | 5/2003 | Pressman et al. |
| 2003/0235518 | A1 * | 12/2003 | Shea et al. |
| 2004/0002163 | A1 * | 1/2004 | Reinhardt et al. |
| 2006/0045806 | A1 * | 3/2006 | Winther et al. |
| 2006/0078463 | A1 * | 4/2006 | Shea et al. |

OTHER PUBLICATIONS

Tecan HS 4800 Microarray Hybridization Application Note, pp. 1-5, Tecan USA http://www.tecan.com.

Tecan HS 4800 Hybridization Station Operating Manual, Doc. Part No. I 114 901, Dec. 2002.

GeneTAC (TM) HvbStation FAQ, Genomic Solutions, Inc.; http://www.genomicsolutions.com/genomics/hvbfaq.html.

GeneTAC (TM) Hyb-4 Hybridization Station, Genomic Solutions, Inc.; http://www.genomicsolutions.com/genomics/hybrid.html.

GeneTAC (TM) Hvb Station User's Manual, Genomic Solutions Inc., Version 3.0, Feb. 24, 2000.

Automated Slide Processor (ASP) User's Guide; Amersham Pharmacia Biotech No. 18-1147-50, edition AA, Sep. 2000.

DakoCytomation Artisan Staining Stytem Product Information, DakoCytomation http://www.dakocytomation.us/prod.

Thermo Hybaid OmniSlide Modular System, Thermo Electron Corporation http://www.thermohybaid.com/cgi-bin.

Thermo Hybaid OmniSlide In Situ Hybridisation System User Operating Manual; Thermo Electron Corporation, Issue 6.0, Mar. 2001; pp. 1-84.

Ventana Discovery(TM) System Brochure, Ventana Medical Systems, Inc., Tucson, AZ.

Ventana Discovery(TM)—The Discovery System, Ventana Medical Systems, Inc. http://www.ventanadiscovery.com/product/index.html.

* cited by examiner

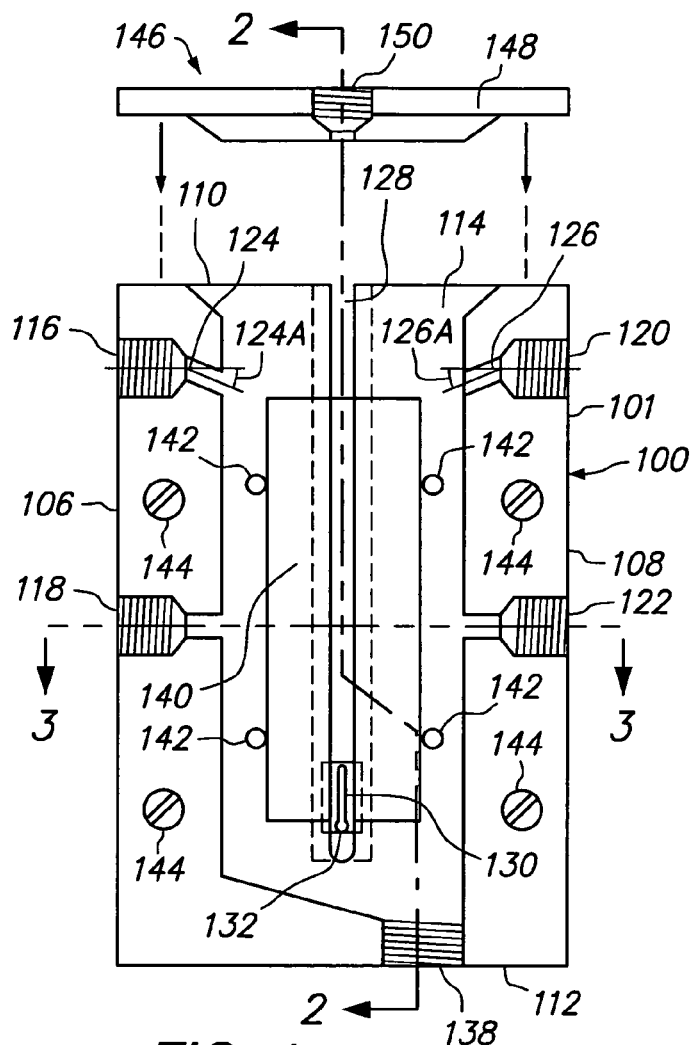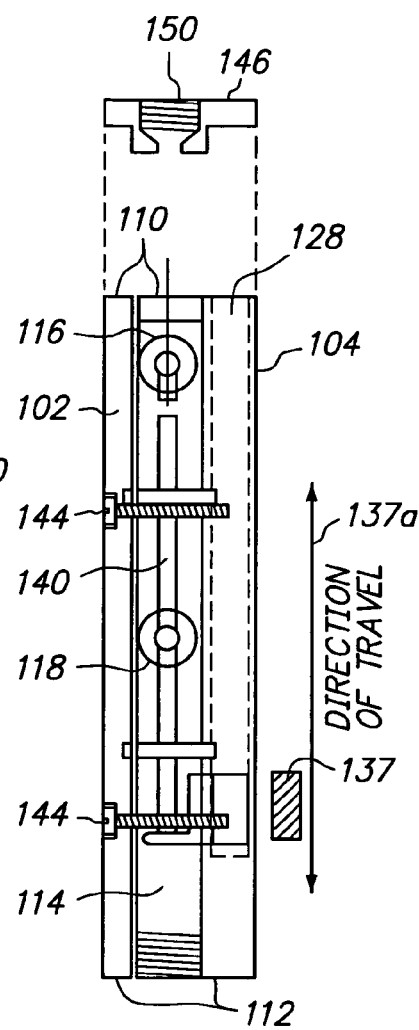
FIG. 1
FIG. 2
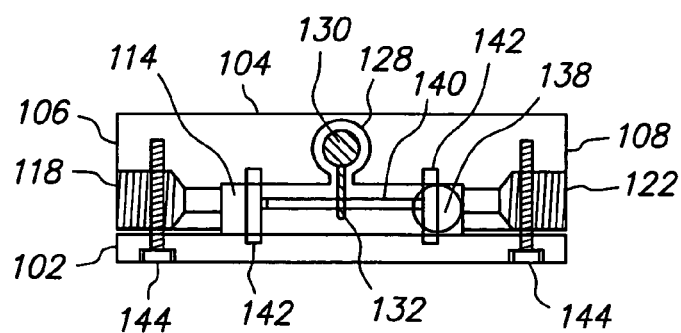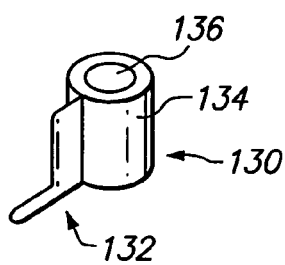
FIG. 3
FIG. 4

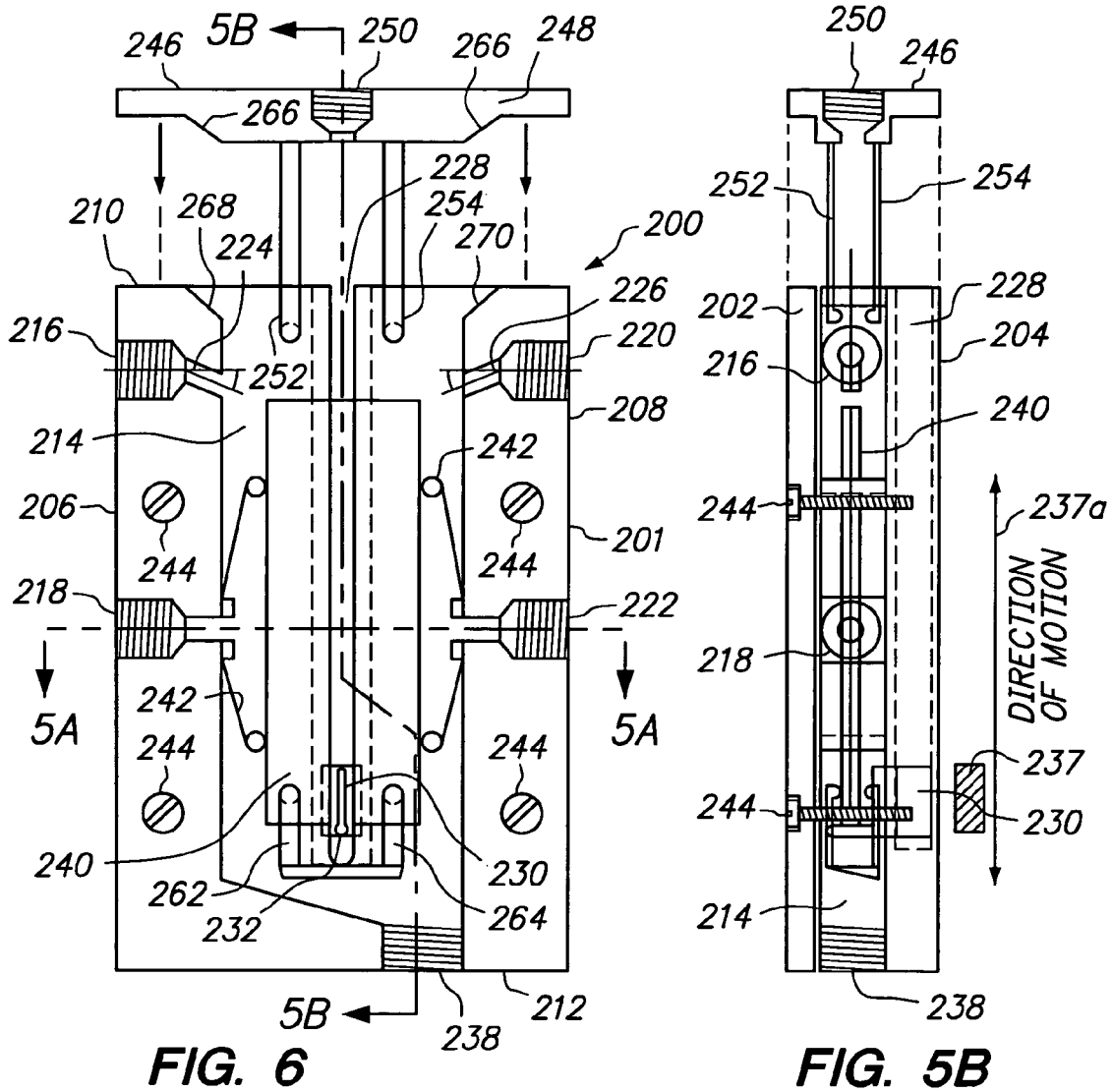
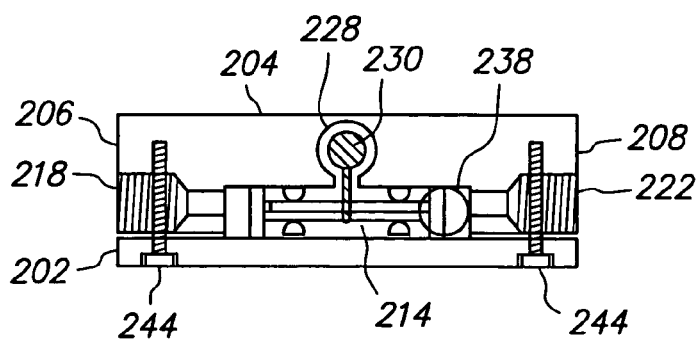
FIG. 5A

APPARATUS FOR SUBSTRATE HANDLING

BACKGROUND OF THE INVENTION

This invention relates generally to apparatus and methods for use in conducting chemical, including biochemical, reactions on a solid substrate. More particularly, the invention relates to apparatus and methods for conducting various processing steps that are part of such chemical reactions. The invention has utility in fields relating to biology, chemistry and biochemistry. The invention has particular application to the area of analyzing the results of hybridization reactions involving nucleic acids and proteins.

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. New methods of diagnosis of diseases, such as AIDS, cancer, sickle cell anemia, cystic fibrosis, diabetes, muscular dystrophy, and the like, rely on the detection of mutations present in certain nucleotide sequences. This paradigm shift has lead to an increasing need within the life science industries for more sensitive, more accurate and higher-throughput technologies for performing analysis on genetic material obtained from a variety of biological sources.

Unique or misexpressed nucleotide sequences in a polynucleotide can be detected by hybridization with a nucleotide multimer, or oligonucleotide, probe. Hybridization reactions between surface-bound probes and target molecules in solution may be used to detect the presence of particular biopolymers. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen-bonded structure with a complementary nucleic acid sequence has been employed as an analytical tool in molecular biology research. An oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present.

Such reactions form the basis for many of the methods and devices used in the new field of genomics to probe nucleic acid sequences for novel genes, gene fragments, gene variants and mutations. The ability to clone and synthesize nucleotide sequences has led to the development of a number of techniques for disease diagnosis and genetic analysis. Genetic analysis, including correlation of genotypes and phenotypes, contributes to the information necessary for elucidating metabolic pathways, for understanding biological functions, and for revealing changes in genes that confer disease. Many of these techniques generally involve hybridization between a target nucleotide sequence and a complementary probe, offering a convenient and reliable means for the isolation, identification, and analysis of nucleotides. The surface-bound probes may be oligonucleotides, peptides, polypeptides, proteins, antibodies or other molecules capable of reacting with target molecules in solution.

Direct detection of labeled target nucleic acid hybridized to surface-bound polynucleotide probes is particularly advantageous if the surface contains a mosaic of different probes that are individually localized to discrete, known areas of the surface. Such ordered arrays of probes are commonly referred to as "biochip" arrays. Biochip arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective attachment to matching probe sites takes place. The array is then washed and imaged so as to reveal for analysis and interpretation the sites where attachment occurred.

One typical method involves hybridization with probe nucleotide sequences immobilized in an array on a substrate having a surface area of typically less than a few square centimeters. The substrate may be glass, fused silica, silicon, plastic or other material; preferably, it is a glass slide, which has been treated to facilitate attachment of the probes. The mobile phase, containing reactants that react with the attached probes, is placed in contact with the substrate, covered with another slide, and placed in an environmentally controlled chamber such as an incubator. Normally, the reactant targets in the mobile phase diffuse through the liquid to the interface where the complementary probes are immobilized, and a reaction, such as a hybridization reaction, then occurs. Preferably, the mobile phase targets are labeled with a detectable tag, such as a fluorescent tag, or chemiluminescent tag, or radioactive label, so that the reaction can be detected. The location of the signal in the array provides the target identification. The hybridization reaction typically takes place over a time period of seconds up to many hours.

Biochip arrays have become an increasingly important tool in the biotechnology industry and related fields. These binding agent arrays, in which a plurality of binding agents are synthesized on or deposited onto a substrate in the form of an array or pattern, find use in a variety of applications, including gene expression analysis, drug screening, nucleic acid sequencing, mutation analysis, and the like. Substrate-bound biopolymer arrays, particularly oligonucleotide, DNA and RNA arrays, may be used in screening studies for determination of binding affinity and in diagnostic applications, e.g., to detect the presence of a nucleic acid containing a specific, known oligonucleotide sequence.

Polynucleotide microarrays may be subjected to hybridization reactions in the following manner. In one approach polynucleotide target material is prepared by purifying, labeling and suspending it in liquid hybridization buffer, which is typically a solution of lithium lauryl sulfate, LiCl, Li-MES, EDTA and Triton X-100 in various percentage concentrations. This hybridization buffer mix is applied to the active surface of the microarray and the microarray is incubated for a period of time, typically about 18 hours at an elevated temperature of about 40 to about 70° C. Following incubation, the hybridization buffer is removed from the microarray surface and the non-specifically bound target material is washed away in one or more wet process steps using one or more wash reagents of varying stringency. Stringency is controlled typically through salt concentration and reagent temperature. Following the last wash step, the surfaces of the microarray are dried. The microarray is fluorescently scanned and the resulting image is analyzed to determine the degree of probe-target binding.

The pattern of binding by target molecules to biopolymer probe spots on the microarray or biochip forms a pattern on the surface of the biochip and provides desired information about the sample. Hybridization patterns on biochip arrays are typically read by optical means, although other methods may also be used. For example, laser light in the Agilent Technologies Inc. Microarray Scanner excites fluorescent molecules incorporated into the nucleic acid probes on a biochip, generating a signal only in those spots on the biochip that have a target molecule bound to a probe molecule, thus generating an optical hybridization pattern. This pattern may be digitally scanned for computer analysis. Such patterns can be used to generate data for biological assays such as the identification of drug targets, single-nucleotide polymorphism mapping, monitoring samples from patients to track their response to treatment, and assess the efficacy of new treatments.

The process steps associated with hybridizing microarrays (incubation, washing and drying) are commonly performed manually using conventional molecular biology/chemical laboratory apparatus and techniques. The above techniques are particularly applicable for microscope-slide-like microarrays. Incubation is done statically or with vibrating motion in heated water baths or with gentle rotational mixing motion in dry incubators. Washing is done using histology slide staining glassware, open dishes and tubs, and hot plates with magnetic stirrers to agitate the wash buffer. Drying is done by applying a stream of compressed dry gas (air or nitrogen) to the surface of the microarray or by centrifuging the microarray.

Significant process variability is inherent in the manual hybridization of microarrays, especially manual washing and drying. This leads to poor reproducibility. Manual methods result in overall degraded microarray performance as evidenced by variable sensitivity, poor spatial uniformity, higher background levels, poor background level spatial uniformity, reduced expressed-signal-to-background ratio, and variable specificity. Specifically, manual methods are burdened by the following characteristics: a) multiple repetitive process steps which are labor intensive, b) significant touching and handling of the individual microarray support substrates as they move from one process step to the next, c) exposure of the microarray support substrates to the surrounding laboratory atmosphere as they are transferred from one process step to the next, d) inability to keep substrates completely wet (submerged) at critical times during processing, e) exposure of the microarray support substrates to wash reagents of indeterminate stringency and concentration due to poorly controlled wash bath temperatures (wash baths are commonly heated and stirred on laboratory hot plates without the benefits of closed-loop temperature control), f) loosely controlled wash step duration and variability of wash timing due to the difficulty of manually managing a time-staggered queue of microarray support substrates as they are processed, g) gradual degradation of wash reagents due to contaminant build-up caused by processing multiple support substrates with a single replenishment of reagent, which is aggravated by the inconvenience of manually replacing pre-heated or pre-cooled reagents.

The process steps associated with hybridizing microarrays (incubation, washing and drying) have been automated to varying degrees by laboratory instrumentation designers. There are numerous examples of commercially available hybridization stations. In general, the purpose of every commercial automated hybridization station, whether for packaged microarrays or for microscope-slide-like microarrays, is to provide consistent, regimented incubation, washing and drying. The Fluidics Station from Affymetrix, Inc., provides automated hybridization for their GeneChip® series of packaged microarrays. The GeneChip® series of microarrays represent a 'closed system' since they are mechanically incompatible with conventional microscope-slide-like microarrays. Some currently available hybridization stations capable of processing microscope-slide-like microarrays are: the Automatic Slide Processor (ASP) from Amersham Pharmacia Bio-Science; the GeneTAC™ HybStation and Hyb4 hyb-station, both from Genomics Solutions Inc.; the TECAN HS-Series HybStation from TECAN (Austria); the a-Hyb™ from Memorec Stoffel GmbH; the DISCOVERY™ system from Ventana; and the OmniSlide Modular System from Hybaid UK (a Themmo BioAnalysis Company).

Most of the commercially available hybridization stations have one or more limitations such as: poor drying of microarrays by controlled fluid draining, by dry gas injection or by hybridization chamber evacuation; inability to handle multiple isolated arrays per substrate; poor accommodation of wide range of slide dimensions; lack of visual inspection during sample loading; no provision for pre-heating or pre-cooling reagent reservoirs, poor or no reagent cooling capability, reduced wash effectiveness due to moderate to low volume washing; poor dilution of non-specifically bound target material and spent wash buffer residue due to low fluid volumes.

In addition, hybridization stations have been disclosed in U.S. patent application Ser. No. 09/919,073, filed Jul. 30, 2001 (Donlon, et al.), entitled "Sample Processing Apparatus and Methods," and in U.S. Patent Application 2000/004,6702 A1, filed 19 Jun. 2001 (Schembri), entitled "Devices for Performing Array Hybridization Assays and Methods of Using the Same."

In addition, hybridization designs are disclosed in patent application WO 01/32934 A2, Hybridization Station, assigned to Arcturus Engineering Inc, and patent application WO 01/31347 A1, Modular Automated Sample Processing Apparatus, assigned to SmithKline Beecham PLC.

There is a need for an apparatus and methods for conducting processing steps in chemical reactions, particularly on a non-porous substrate, which may avoid or alleviate one or more of the aforementioned limitations.

SUMMARY OF THE INVENTION

One embodiment of the present invention is a device for conducting processing steps on a substrate comprising a plurality of biopolymer features on a surface thereof. The device comprises a housing comprising a housing chamber with an opening in the housing adapted for insertion of a substrate having a surface comprising a plurality of biopolymers into the housing chamber. The device also comprises a fluid separation mechanism for separating fluid from contact with the substrate in a controlled manner. Normally, the device has at least one inlet in fluid communication with the housing chamber and at least one outlet in fluid communication with the housing chamber.

Another embodiment of the present invention is a device for conducting processing steps on a substrate that has a surface that comprises a plurality of biopolymer features. The device comprises a housing comprising a housing chamber. The housing comprises an opening through which a substrate may be inserted into the housing chamber. The device also comprises a lift mechanism for lowering the substrate into and lifting the substrate out of the housing chamber in a controlled manner. At least one inlet is in fluid communication with the housing chamber and at least one outlet is in fluid communication with the housing chamber.

Another embodiment of the present invention is a device for conducting processing steps on a substrate comprising a plurality of biopolymer features on a surface of the substrate. The device comprises a housing comprising a housing chamber. The housing comprises an opening through which a substrate may be inserted into the housing chamber. The device also comprises a fluid transfer mechanism for adding and/or removing fluid from the housing chamber in a controlled manner. The fluid transfer mechanism may include pumps, valves, reagent reservoirs, heat exchangers and the like. At least one inlet is in fluid communication with the housing chamber and at least one outlet is in fluid communication with the housing chamber.

Another embodiment of the present invention is a method for conducting a processing step on a substrate comprising a surface with a plurality of biopolymer features. The surface is brought into contact with a processing fluid; and, then, the surface is removed from contact with the fluid in a controlled manner at a rate that preserves the integrity of the fluid meniscus at the atmosphere-fluid interface substantially eliminating droplet formation of the fluid on the surface of the substrate, resulting in a substantially dry substrate surface.

Another embodiment of the present invention is a method for performing a step of a chemical reaction on the surface of a substrate. A substrate is inserted into a device as described above and a fluid reagent for performing the step of the reaction is introduced into the housing chamber by means of the inlet. The fluid reagent is removed from the housing chamber by means of the outlet in a controlled manner at a rate that preserves the integrity of the fluid meniscus at the atmosphere-fluid interface substantially eliminating droplet formation of the fluid on the surface of the substrate, resulting in a substantially dry substrate surface. A tilting mechanism, promotes the removal of fluid from the chamber and droplets from the lower-most edges of the substrate. The optimum tilt angle depends on the size and geometry of the substrate and chamber.

Another embodiment of the present invention is a method for performing a step of a chemical reaction on the surface of a substrate. A substrate is inserted into a device as described above and a fluid reagent for performing the step of the reaction is introduced into the housing chamber by means of the inlet. The fluid reagent is removed as described above in a controlled manner. Concomitant with the controlled removal of fluid reagent, the volume above the fluid level in the chamber is filled with known gas and an organic vapor. Such vapor creates a surface tension gradient at the atmosphere-fluid interface to preserve the integrity of the fluid meniscus, substantially eliminating droplet formation as the fluid recedes. The introduction of organic vapor is beneficial when processing substrates with predominantly hydrophilic surfaces. The chamber is tilted as describe above to promote the removal of fluid from the chamber and droplets from the lower-most edges of the substrate.

Another embodiment of the present invention is a method for performing a step of a chemical reaction on the surface of a substrate. A substrate is inserted into a housing chamber of a device as described above. A fluid reagent for performing the step of the chemical reaction is introduced into the housing chamber by means of the inlet. The substrate is lifted from the housing by means of the lifting mechanism in a controlled manner at a rate that substantially eliminates droplet formation of the fluid on the surface of the substrate.

Another embodiment of the present invention is a method for performing a step of a chemical reaction on the surface of a substrate. A substrate is inserted into a device as described above and a fluid reagent for performing the step of the reaction is introduced into the housing chamber by means of the inlet. The fluid reagent is removed from the housing chamber by means of the outlet in a controlled manner at a rate that preserves the integrity of the fluid meniscus at the atmosphere-fluid interface substantially eliminating droplet formation of the fluid on the surface of the substrate, resulting in a substantially dry substrate surface.

In an alternative embodiment of the aforementioned methods for performing a step of a chemical reaction, the substrate may be lifted out of the housing chamber substantially concomitantly with the removal of the fluid reagent from the housing chamber.

Another embodiment of the present invention is an apparatus for conducting a processing step of a chemical reaction involving an array of biopolymers on the surface of a substrate. The apparatus comprises one or more devices as described above, one or more fluid reagent reservoirs in fluid communication with one or more of the devices, a tilt mechanism for controlling the orientation of each of the devices, one or more pumps for controlling the flow of fluid reagents into each of the devices, at least one heat exchanger for controlling the temperature of the fluid reagents, and a portion of a lifting mechanism external to the devices. The apparatus may also comprise a transfer mechanism for moving a substrate to and from the devices and/or a thermally insulating member around at least a portion of each of the devices.

BRIEF DESCRIPTION OF THE DRAWINGS

FIG. 1 is a front view of a flow device in accordance with the present invention.

FIG. 2 is a side view of the device of FIG. 1.

FIG. 3 is a top view of the device of FIG. 1 without a cap in place on the top of the device.

FIG. 4 is a perspective view of the lifting paw portion of a lifting mechanism for use in the device of FIG. 1.

FIG. 5A is a top view of the device of FIG. 6 without a cap in place on the top of the device.

FIG. 5B is a side view of the device of FIG. 6.

FIG. 6 is a front view of another flow device in accordance with the present invention.

DETAILED DESCRIPTION OF EMBODIMENTS OF THE INVENTION

Figure 7:
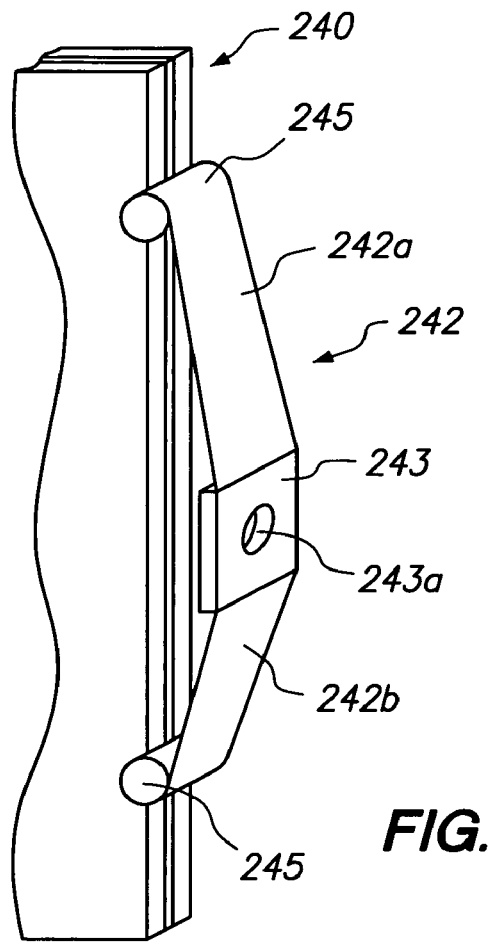
FIG. 7 is a partial view depicting a biasing member of the device of FIG. 6.

Embodiments of the present invention comprises devices, apparatus and methods to conduct washing and drying steps on microarray substrates according to one or more user-specified protocols. The devices, apparatus and methods may be conveniently carried out automatically. In one aspect the present devices are flow devices such as flow cells. The devices have an opening for insertion of a substrate into the device, a sealing member such as a cap, as well as one or more inlets and one or more outlets for introduction and removal of fluid reagent(s) and one or more inlets for the introduction of gases or vapors. The devices comprise a mechanism that provides for separating a surface of the substrate from a fluid reagent in a controlled manner so that the integrity of the fluid meniscus at the atmosphere-fluid interface is preserved and droplet formation on the surface of the substrate is substantially eliminated resulting in a substantially dry substrate surface.

In one embodiment the present devices comprise a substrate elevator, fluid and gas control valves, a fluid circulation pump, reagent heat-exchanger and associated sensors, and temperature controller.

In one embodiment an apparatus in accordance with the present invention comprises one or more of the present flow devices, multiple reagent reservoirs with pre-heating and pre-cooling capability and associated fluid routing valves, liquid waste collection reservoir, solvent vapor generator to assist drying hydrophilic-surfaced substrates, and microprocessor, embedded real-time software and I/O interface electronics to control the sequence of operations of the invention. As a result of the aforementioned hardware and software the various components of the present devices and present apparatus are adapted to carry out the functions specified.

In one embodiment a device of the invention comprises a housing comprising a housing chamber. The housing comprises an opening through which a substrate may be inserted into the housing chamber. A sealing member such as a cap may be applied to seal the housing chamber to prevent unintended fluid or gas leakage. The device also comprises a lift mechanism for lifting the substrate out of the housing chamber in a controlled manner. At least one inlet is in fluid communication with the housing chamber, at least one outlet is in fluid communication with the housing chamber and at least one inlet is in gaseous communication with the housing chamber.

As mentioned above, a flow device of the present invention comprises a housing having a cavity or housing chamber therein. The housing generally comprises a frame with suitable cross members for structural strength where necessary. One or more walls of the housing may be formed from a solid material that gives structural strength to the housing and provides for a frame. The structural strength must be sufficient to permit various manipulations including pressure changes, containment of fluids, support of the biopolymer substrate, chemical corrosion and mechanical abrasion resistance and the like that occur in the use of the present device. There should also be sufficient structural strength so that various moving parts may be mounted within the housing chamber. Such materials include, for example, metal, plastic, composite materials, containment of fluids, support of the biopolymer substrate, chemical corrosion and mechanical abrasion resistance and the like. The housing may be constructed from thermally insulated materials that are chemically inert with respect to the fluid reagents used in the device. Such materials include, for example, stainless steel, glass, ceramic, and plastics such as nylon and polypropylene and the like. The housing may be surrounded with a thermally insulating jacket to maintain it and its fluid contents at a stable temperature.

In general, the housing has a top wall, a bottom wall, a front wall, a rear wall and two sidewalls. The above designation of the walls is based on the orientation of the device during operation where the device is disposed in a substantially vertical position such that its longitudinal axis is maximized. By the phrase "substantially vertical position" means that the device is disposed at a 90-degree angle with respect to the horizon or within about 45 to about 135 degrees, usually, within about 70 to about 90 degrees, from the horizon. As mentioned above, the housing chamber may also comprise a sealing member such as, for example, a cap, lid, or the like, that seals the housing chamber to prevent unintended fluid or gas leakage.

In one approach in the fabrication of the present device, front and rear walls may be secured together in a sealed relationship. Each wall comprises hollowed out regions corresponding to the various features of the housing chamber such as a main chamber, inlet channels, outlet channels, a shaft for a magnetic lifter as explained in more detail below, locations for alignment and guide elements, substrate mechanical supports, substrate separator fixtures and so forth. When the two walls are sealingly mated, the housing chamber with all of its desired features is obtained. The two walls may be secured together by fasteners such as, e.g., screws, bolts, pins, clamps etc., by welding, by adhesives, or cast as one block and machined out and the like. In some circumstances, a gasket may be used to surround the mated areas to provide for a seal that is fluid tight. The sculpting of the preformed walls may be made by techniques such as, for example, molding, etching, machining, casting and so forth.

The dimensions of the housing chamber are dependent on the dimensions of the substrate, the dimensions of which may vary depending on the nature of the substrate. In general, the internal dimensions of the housing chamber should be sufficiently large enough so that the housing chamber can accommodate approximately 3-5 times the cubic volume of the substrate plus the volume of the other elements of the present device. The above factors govern the dimensions of the housing chamber. For example, the substrate may be about 1 to about 10 inches or more in length, usually, about 1 to about 8 inches in length, and may be 1.5 to about 5 inches in length. The width of the substrate may be about 0.2 to about 10 inches in width, usually, about 0.5 to about 5 inches in width and may be about 0.5 to about 3 inches in width. The substrate is about 0.1 to about 10 mm, usually, about 0.2 to about 5 mm, more usually, about 0.5 to about 3 mm, in thickness. A standard size microscope slide is usually about 3 inches in length, 1 inch in width and 1 mm thick. Other dimensions of the substrate are possible depending on the use and the like.

In one embodiment of a device in accordance with the present invention at least a portion of one wall of the housing may have a viewing area for viewing a surface of the substrate that is inserted therein. Usually, this viewing area is in the form of a window in the wall of the housing. The window may be manufactured from any material that will permit viewing of the surface of the substrate. Such materials may be transparent is some wavelengths and opaque in others to prevent degradation of the biochip substrate by ambient light during processing. Such materials include by way of example and not limitation, transparent plastic, glass, and so forth. The viewing area is not essential to the operation of the invention, but it permits convenient observation of the filling and emptying of the reagent chamber. With an appropriate sensor, the filling and emptying operations may be automated and monitored. The portion of the wall of the housing that permits viewing the surface of a substrate may be incorporated into the wall by suitable means such as screws, bolts, adhesives, bonding, welding, double-shot molding and so forth.

The housing has an opening, which is adapted for insertion of a substrate into the housing chamber. The opening may be formed, for example, when front and rear walls are mated to form the present device. The opening permits the substrate to be inserted into the interior of the housing chamber. The dimensions of the opening in the housing for insertion of the substrate are dependent on the dimensions of the substrate. In general, the opening in the wall of the housing should be sufficiently large enough to permit the substrate be inserted into and removed from the housing chamber without interference with the sides of the opening. The opening should not be larger than necessary to permit the insertion and removal of the substrate.

The present device has at least one inlet in fluid communication with the housing chamber; at least one outlet is in fluid communication with the housing chamber and may include at least one inlet in gaseous communication with the housing chamber. The number of fluid inlets and outlets is dependent on the desired fluid fill and removal rates, the desired fluid exchange rate when simultaneously filling and removing fluids, the optimum substrate irrigation pattern and so forth. Usually, the number of fluid inlets is about 1 to about 4, more usually, at least 2, and the number of outlets is about 1 to about 4, more usually, at least one. The inlet may be used for introducing fluid reagents into the reagent chamber. Fluid reagents may be removed from the housing chamber through the outlet or, in some cases, the inlet. If the fluid reagents are removed through the inlet, the outlet may be used for venting the interior of the housing chamber. The number of gas inlets, in addition to the fluid inlets mentioned above, is about 1 to about 2, at least 1. Both the fluid inlet and the outlet may be in the same wall of the housing or each may be in a different wall of the housing. Both the inlet and the outlet are in fluid communication with the housing chamber. The dimensions of the fluid inlets and outlets are determined by the fluid flow rates. Usually, the dimensions of the inlets are about 0.05 inch to 0.5 inch diameter, more usually 0.125 to 0.25 inch diameter and the dimensions of the outlets are about 0.05 inch to 0.5 inch diameter, and usually larger than the inlet diameters. The gas inlet is may be in the same wall of the housing as the fluid inlets, usually it is above the level of the upper-most fluid inlet or outlet. The dimensions of the gas inlets are determined by the vapor flow rates.

In one approach the inlet and the outlet may each be connected to tubing. The dimensions of the tubing are generally dependent on the dimensions of the reagent chamber. The dimensions of the tubing must be sufficient to deliver and remove the desired amounts of fluid reagents to and from the reagent chamber. Appropriate connectors as known in the art may be used to connect the tubing to the inlet and the outlet. The tubing provides for fluid communication between the interior of the housing chamber and other elements and receptacles and the like such as, e.g., fluid reagent reservoirs, waste fluid reservoirs, gas sources, valves, heat exchangers, and so forth.

The inlet and the outlet may be disposed at or near the corners of the housing. For example, the inlet may be disposed in a corner of the housing opposite a corner in which the outlet is disposed. In general, the inlet and the outlet are disposed to provide for efficient entry into and removal of fluid reagents from the housing chamber in accordance with the principles of the present invention. In one embodiment an inlet may be at or near an upper corner of the housing in a sidewall and an outlet may be in the lower corner of the housing opposite the inlet in a bottom wall of the housing. In one embodiment the bottom of the housing chamber is sloped toward the outlet to provide for more efficient removal of fluid reagents from the housing chamber. The percent of sloping of the bottom of the housing chamber is about 1 to about 50%, usually, about 5 to about 20%.

The flow device of the present invention may comprise separators for separating a substrate from a cover slide. In some instances a cover slide is placed over the surface of the substrate on which chemical reactions are to be carried out, thus, forming a sandwich. When this substrate-cover slide sandwich is inserted into the present flow device, a separator assists in separating the substrate and the cover slide so that fluid reagents may contact the surface of the substrate on which the chemical reactions, including processing steps, are to occur.

The separator may comprise biasing members, which are disposed on either side of, and engage, the outer surfaces of the substrate-cover slide sandwich. Between the biasing members is a wedge, which inserts between the substrate and the cover slide thereby causing separation. The dimensions of the wedge should be such as to cause sufficient separation of the substrate and the cover slide so that fluid reagents can contact the surface of the substrate on which chemical reactions occur. The spacing between the substrate surface and the cover slide for this purpose is about 0.05 mm to about 2 mm, usually, about 0.2 mm to about 0.6 mm. In one embodiment the wedge is a substantially rigid member with a pointed tip and may be fabricated from plastic, stainless steel, ceramic, glass and the like. By "substantially rigid" is meant that the member is rigid enough to insert between the substrate and the cover slide and cause separation of the substrate and the cover slide. The length of the wedge is usually about 1 mm to about 5 mm. The biasing members may comprise a pliable material such as plastic, spring metal and the like. The area of the biasing members that contacts the outer surfaces of the substrate-cover slide sandwich may be beveled, rounded, chamfered or the like. The biasing members may be in the form of finger-like projections, leaf springs, spring-loaded guide pins and the like. The length of the biasing member is usually about 0.5 inch to about 3 inches.

One or more separators may be employed near the bottom of the housing chamber to engage the substrate-cover slide sandwich as it is inserted into the housing chamber. Furthermore, one or more separators may be employed near the top of the housing chamber as part of a sealing member such as an end cap that may be secured to the top of the housing after the substrate-cover slide sandwich has been inserted into the housing chamber. The dimensions of the cap are governed by the dimensions of the housing. The cap may be removably secured to the top of the housing by means of screws, pins, clamps, springs, friction-fit and the like. The cap may include an angled portion that inserts into a corresponding angled recessed portion of the upper part of the housing of the present device in order to channel un-contained fluids into the chamber.

The present device may also comprise a lifting mechanism for lifting a substrate into or out of the housing chamber in a controlled manner. The lifting mechanism is adapted to lift the substrate out of the housing chamber at a rate that preserves the integrity of the fluid meniscus at the atmosphere-fluid interface substantially eliminating droplet formation of fluid reagent at least on the surface of the substrate that comprises the chemical compounds resulting in a substantially dry substrate surface. By the phrase "preserves the integrity of the fluid meniscus at the atmosphere-fluid interface substantially eliminating droplet formation" is meant that the existing surface tension of the fluid in conjunction with the level of hydrophobicity or hydrophilicity of the substrate surface discourages or avoids the formation of isolated droplets separate from the major fluid mass. By the phrase "substantially dry substrate" is meant that residual fluid reagent, if any, remaining on the surface of the substrate should be in the form of a substantially uniform film that is not be more than a few hundreds of microns thick, usually, not more than about 0.1 microns to 1 micron thick. The phrase "substantially uniform" means that the film thickness does not vary by more than about 15%, about 10%, about 5%, about 4%, about 3%, about 2%, about 1%. Thin films less than half the wavelength of visible light visually appear dry. There may be some droplet formation at or near the bottom of the substrate or on the face-edges of the substrate, usually, in an area at the bottom that does not comprise chemical compound features. By the phrase "adapted to" is meant that the lifting mechanism comprises the necessary hardware and software to provide lifting of the substrate into and out of the housing chamber in a controlled manner. The hardware and software includes microprocessor, embedded real-time software and I/O interface electronics to control the lifting mechanism. The lifting mechanism may comprise any number of platforms, fixtures, frames, carriages, gantries, pulleys, chains, cables, lead-screws, belts, electrically-, magnetically- or pneumatically-energized rotary or linear-motors, solenoids or voice-coil actuators, pneumatic or hydraulic cylinders and so forth to accomplish the lifting of the substrate. The lifting mechanism may be, for example, an elevator, lead-screw carriage or linear motor and so forth. The following specific examples are by way of illustration and not limitation.

In one embodiment the lifting mechanism may be an elevator that comprises means for supporting the substrate as well as means for moving the supporting means to lift the substrate. The supporting means may be a supporting member such as a platform that may be of any shape, dimensions and strength to provide sufficient support for the substrate. The platform may have any convenient shape such as, for example, pin, finger, ledge, tab, paw, flange and the like. The supporting member is moved by means for moving the supporting means. The moving means may comprise pulleys, chains, motors, magnets, lead-screws, belts, cables and so forth in any combination to accomplish the desired moving of the platform.

The moving means may be partially or wholly integral with the supporting means or may be partially or wholly independent of the supporting means and the housing. By the term "partially" is meant that the moving means may comprise one or more components that are integral with the supporting means and one or more components that are independent of the supporting means. The dimensions of the supporting member are dependent on the dimensions of the substrate to be supported. The primary consideration is that the substrate can be moved into and out of the housing chamber in a substantially vertical manner. This may be accomplished by having a supporting member that is large enough to support the substrate and maintain the substrate in a substantially vertical orientation with respect to the horizontal. The phrase "substantially vertical" means that the deviation of the orientation from perpendicular to the horizontal does not vary by more than about 15%, about 10%, about 5%, about 4%, about 3%, about 2%, about 1%. In this approach the dimensions of the supporting member are such that the longest dimension of the member is about 80% to about 120%, usually, about 90% to about 110%, that of the dimension of the substrate edge in contact with the supporting member. On the other hand, guide means may be present in the housing chamber to assist in maintaining the substrate substantially vertical. In this latter situation, the supporting member may be about 3% to about 20%, usually, about 5% to about 10% of the dimension of the substrate edge in contact with the supporting member. Guide means include, for example, rollers, pins, biasing members such as, e.g., springs, tabs, fingers, paws and the like. The guide means are usually fabricated from materials that are inert to the fluid reagents used in the present methods. Such materials include, for example, plastic, ceramic, glass, stainless steel and so forth.

In one specific embodiment an elevator comprises a magnetic lifter, in contact with the substrate, constrained to move in a channel or shaft, which is in fluid contact with the interior of the housing chamber, and a lifting carriage external to the housing chamber. The dimensions of the channel or shaft are dependent on the dimensions of the portion of the magnetic lifter that is movable within the channel or shaft. The cross-sectional dimension of the channel should be slightly larger than the cross-sectional dimension of such portion. As a general rule, the channel should be large enough so that it does not interfere with the movement of the portion of the magnetic lifter within the channel. Usually, the channel is about 0.1% to about 25%, more usually, about 0.1% to about 2%, larger than the portion of the magnetic lifter in the channel.

The magnetic lifter comprises a support member integral with a magnetically movable member, which may be a magnet or a magnetically responsive material. In either case, the magnetically movable member is usually encapsulated in, or coated with, a protective material that is inert to the fluid reagents in the housing chamber. Such protective materials include, for example, plastic, polypropylene, ceramic, glass and the like. The application of the protective material to the member utilizes standard procedures well known in the art. If the magnetically movable member is a magnet, it may be, for example, an electromagnet or preferably a permanent magnet so that no additional intrusions into the chamber are required to activate the magnet. If the magnetically movable member is a magnetically responsive member, it is usually fabricated from a material such as soft iron, or mild steel and the like. If the magnetically movable member is a permanent magnet, it is usually fabricated from a material such as Alnico alloy, ceramics, or rare earth metals such as neodymium iron boron (NdFeB), samarium cobalt (SmCo) and the like.

If the magnetically movable member comprises a magnetically responsive member, the lifting member comprises a magnet and a lifting carriage external to the housing chamber. Elements of the lifting member external to the housing chamber are protected from exposure to the fluid reagents. If the magnetically movable member comprises a magnet, the lifting member comprises a magnetically responsive material, permanent- or electro-magnet and a lifting carriage. In any case, the lifting carriage may be a motor-driven lead-screw, track or belt mechanism, and so forth. The lifting carriage is movable in the direction of movement desired for the substrate. Usually, this means that the lifting carriage is movable in a substantially vertical direction. The combination of the magnetically movable member and the lifting member causes the supporting member with the substrate thereon to move inside the housing chamber and either into or out of the housing chamber in a substantially vertical orientation.

In a preferred embodiment from the standpoint of simplicity, the magnetically movable member inside of the housing chamber is a material that is attracted to magnets, i.e., a magnetically responsive member, or one that is a permanent magnet. The lift member is another permanent magnet or an electromagnet. In this embodiment the member external to the housing chamber attracts the member inside of the housing chamber.

As mentioned above, fluid reagents may be separated from the surface of the substrate comprising the chemical compounds by slowly lifting the substrate out of the fluid reagent in the housing chamber in a controlled manner. The rate of lifting of the substrate out of the fluid reagent should be sufficient such that the meniscus at the atmosphere-fluid interface is unbroken essentially eliminating droplet formation on the aforementioned surface of the substrate. The rate of lifting of the substrate out of the fluid reagent and, thus, out of the housing chamber, is usually less than about 5 mm per second, more usually, less than about 2 mm per second. For surfaces that comprise a hydrophobic portion as with chemical compounds synthesized in situ such as polynucleotides including oligonucleotides, the rate of removal of the fluid reagent is usually less than about 2 mm per second, more usually, about 1 mm per second. For surfaces that comprise a hydrophilic portion as with deposited chemical compounds such as deposited polynucleotides including deposited oligonucleotides, the rate of removal of the fluid reagent is usually less than about 1 mm per second, more usually, about 0.2 mm per second. This approach allows for efficient drying of the surface of the substrate without additional drying procedures.

An apparatus in accordance with the present invention may comprise at least one flow device as described above. The apparatus of the present invention may also comprise, and in many instances usually comprises, a pump that may function to assist in introducing fluid reagents into the housing chamber, in recirculating fluid reagents in the housing chamber, in removing fluid reagents from the housing chamber, and the like. The pump may be any convenient pump that will perform the desired function. The pump may also include valve assemblies, manifolds, heat exchangers, and the like to achieve the desired function. Any standard pumping technique for pumping fluids may be employed with the present device. For example, pumping may be by means of a peristaltic pump, a pressurized fluid bed, a positive displacement pump, e.g., a syringe pump, and the like. In one embodiment a sensing element may be employed to follow the filling and emptying of the flow device.

As mentioned above, fluid reagents may be separated from the surface of the substrate comprising the chemical compounds by slowly removing the fluid reagent from the housing chamber in a controlled manner. The rate of removal of the liquid should be sufficient such that the meniscus at the atmosphere-fluid interface is unbroken essentially eliminating droplet formation on the aforementioned surface of the substrate. As explained above, the fluid reagent should be kept as a film on the surface of the substrate as the fluid reagent is removed from the housing chamber. The rate of removal of the fluid reagent is such that the velocity of the receding fluid meniscus is usually less than about 5 mm per second, more usually, less than about 2 mm per second. For surfaces that comprise a hydrophobic portion as with chemical compounds synthesized in situ such as polynucleotides including oligonucleotides, the rate of removal of the fluid reagent is such that the velocity of the receding fluid meniscus is usually less than about 2 mm per second, more usually, about 1 mm per second. For surfaces that comprise deposited chemical compounds such as deposited polynucleotides including deposited oligonucleotides, the rate of removal of the fluid reagent is such that the velocity of the receding fluid meniscus is usually less than about 1 mm per second, more usually, about 0.2 mm per second. This approach also allows for efficient drying of the surface of the substrate without additional drying procedures although in the latter case drying may be promoted by introducing an organic solvent vapor into the housing chamber as the fluid reagent is removed. The organic vapor creates a surface tension gradient in the meniscus against the hydrophilic surface to discourage isolated droplet formation.

In a particular embodiment the pump is a self-priming, positive-displacement peristaltic pump. The pump serves to re-circulate fluid wash reagents during the wash cycle in order to provide agitation action. The aforementioned pump also functions during the drying process step by slowly draining the wash reagent away from the substrate in a controlled manner. The output of the pump is routed to the flow device or to a fluid waste reservoir or other reservoir by the use of appropriate valves controlled by an embedded microprocessor.

Another approach for the controlled removal of fluid reagents from the housing chamber involves the use of one or more valves. The valve should provide for a constant velocity of flow of fluid reagent during the removal. Accordingly, one type of valve that may be employed permits varying the cross-sectional area of the inside passage of the valve with respect to height of fluid reagent in the housing chamber. As the height of the fluid reagent decreases (as fluid reagent is removed), the cross-sectional dimension of the interior of the valve increases. The relationship between cross-sectional dimension and height of fluid should be such as to achieve the desired constant velocity of fluid removal. This relationship may be quantified as follows:

$$\text{Area\_valve} = (\text{Area\_chamber} * \text{Velocity\_meniscus}) / ((2 \, g \, \text{Height meniscus})^{0.5}),$$

where g=force of gravity on earth.

Many of the chemical reactions involving chemical compounds on the surface of the substrate such as, for example, hybridization procedures carried out under prescribed protocols, involve rapid transition from one fluid reagent, e.g., wash reagent, at one temperature to another at a different temperature. To avoid impact on the chemical reactions, fluid reagents re-circulated to the flow device are passed through one or more heat exchangers. The present apparatus comprises at least one heat exchanger. Such heat exchangers may be driven by a chiller unit or a heater unit depending on the protocol selected and the nature of the fluid reagent. The chiller unit or heater unit involved with the heat exchanger operates in concert with sensors and embedded microprocessor control electronics to control, e.g., maintain, the temperature of the fluid reagents throughout the reaction cycle. The use of a fluid heat exchanger provides more responsive and precise temperature control of the fluid reagents than controlling the temperature of the entire flow device. Control of the temperature of the fluid reagents is realized by a system of heat exchangers, pumps, valves, and electronic and computer control. Constructing the flow device from thermally non-conductive materials such as plastic, ceramic or glass and by thermally isolating and insulating the flow device from the ambient further enables maintenance of temperature.

The apparatus of the invention may also comprise a tilt mechanism or a rotating mechanism. During certain steps of the chemical reactions, the flow device operates in an upright, or substantially vertical, orientation. During removal of fluid reagent from the housing chamber in accordance with the present invention, the flow device is tilted about 5 degrees to about 45 degrees, usually, about 15 degrees to about 45 degrees, from the vertical in order to position the substrate so that one of its corners is at a point lower than all the other of its corners. This orientation during removal of fluid reagents in a controlled manner assists in driving any fluid droplets, which might have a tendency to form during the final stages of fluid reagent removal, to a single corner of the substrate where they are most easily removed with the receding fluid reagent. Usually, the tilt mechanism is motor driven. The tilt mechanism may take the form of electromechanical or pneumatic rotary motor, rotary solenoid or actuator, solenoid or linear motor driven crank or linkage assembly and the like.

The present apparatus also comprises one or more fluid reagent reservoirs. The number of fluid reagent reservoirs is dependent on the nature of the chemical reactions and the nature of the processing steps involved. Usually, the number of fluid reagent reservoirs is 1 to about 10, more usually, 1 to about 5. The fluid reagent reservoirs may be affixed to the main platform on which the flow devices of the invention are mounted. Any fluid dispensing reservoir may be employed that dispenses fluids such as water, aqueous media, organic solvents and the like. The fluid reagent reservoirs are usually controlled by a suitable valve assembly and may also comprise a manifold as well as a means for delivering predetermined quantities of fluid reagent to the flow device. The fluid reagent reservoirs may also incorporate sensors to monitor their volumes.

An apparatus in accordance with the present invention may also comprise a transport element for delivering the substrate to the flow device. A suitable transport element may comprise a main arm and an end portion that contacts and engages a surface of the substrate. In one embodiment the transfer element is vacuum activated. The transfer element may comprise at least two prongs and may be in the form of a fork. Other embodiments of the transfer element include, for example, grasping elements such as movable finger-like projections, and the like. The transfer element is usually part of a transfer robot that comprises a robotic arm that is capable of transferring the substrate to and from the flow device. In one embodiment a transfer robot is mounted on the main platform. The transfer robot may comprise a base, an arm that is movably mounted on the base, and an element for holding the support during transport that is attached to the arm. The action of such a transfer robot may be controlled by a microprocessor, embedded real-time software and I/O interface electronics, which conveniently may be the same that controls the sequence of operations of the invention.

An apparatus of the invention may also comprise one or more reaction chambers where some of the reactions are carried out prior to the processing steps that are conducted in the present flow devices. The reaction chambers may be of any form suitable for conducting the desired reactions. In one embodiment the reaction chambers are hybridization chambers. Such hybridization chambers support the substrate surface holding the oligonucleotides in fluid communication with hybridization reagents. Furthermore, such hybridization chambers may be heated to an elevated temperature in an incubator and mixed to promote the chemical reactions. Such hybridization chambers may have the property that they are easily disassembled by mechanical means to extract the contained oligonucleotide support surface. The aforementioned transfer mechanism may be employed to transport a substrate from a reaction chamber to a flow device of the present invention.

As mentioned above, the present flow devices assist in drying the surface of a substrate. By "drying the surface" is meant removal of fluid reagent from the surface so that the fluid film is not more than about a few hundreds of a micron thick, usually, not more than about 0.1 micron to about 1 micron thick. Thin films less than half the wavelength of visible light visually appear dry. With hydrophobic surfaces sufficient drying is obtained by slow controlled lifting of the substrate out of the fluid reagent and/or slow controlled removal of the fluid reagent from contact with the surface. The volume of the housing chamber displaced by the exiting fluid reagent is filled with a dry gas such as air or nitrogen as the fluid reagent recedes.

Hydrophilic surfaces on the substrates are dried in a manner similar to that for the hydrophobic surfaces and are usually assisted by introduction of an organic solvent vapor into the housing chamber (Marangoni Effect) to create a surface tension gradient in the at the meniscus of the fluid reagent. The fluid reagent is slowly drained from the housing chamber and the volume displaced by fluid reagent is filled with organic vapor in a carrier gas. The organic solvent vapor is usually provided by a vapor source that is part of the present apparatus and external to a flow device of the invention. The organic solvent vapor may be obtained from a commercial source in an appropriate container or it may be generated prior to and during its use by a vapor generator. In one approach for a solvent vapor generator, inert gas at relative flow rate of about 100 mL/minute to about 5 L/minute is bubbled into a reservoir of solvent to produce a saturated solvent vapor, which is routed to an inlet in the top wall of the present device. Optionally, an inlet in a sidewall of the device may be employed or an inlet in a cap that is secured to the top of the present device may be used.

The solvent may be, for example, an organic solvent having the appropriate volatility such as, by way of illustration and not limitation, oxygenated organic solvents of from 1 to about 10, more usually from 1 to about 5, carbon atoms, including alcohols such as methanol, ethanol, propanol, diacetone alcohol, etc., ethers such as tetrahydrofuran, ethyl ether, propyl ether, etc., and the like. The inert gas may be, for example, nitrogen, argon, neon, and the like. The solvent vapor in the housing chamber is typically below the saturated vapor pressure. At the saturated vapor pressure, the solvent vapor condenses on the substrate as it is removed from the fluid reagent and on the inner walls of the housing chamber. This situation is to be avoided. Typical ranges for the solvent vapor in the housing chamber above the fluid reagent surface are in the range 0.2 to 0.9, usually between 0.5 and 0.9, of the solvent's saturated vapor pressure. Once fluid reagent has been removed from the housing chamber, the solvent vapor is purged from the housing chamber usually by continued introduction of inert gas without organic component.

The devices and apparatus of the present invention may be controlled by a microprocessor with suitable I/O interface electronics and related embedded real-time control software. The architecture of the control electronics includes microprocessor and core set of I/O interface electronics for controlling the 'shared' portions of the apparatus (control panel, indicators, reagent reservoirs, vapor and gas sources, temperature and fluid level controls, etc). I/O interface electronics may be dedicated to each of the flow devices (elevator drives, tilt motor, valves, peristaltic pump, heat-exchanger heater and cooler, related sensors such as temperature sensors, fluid level sensors, etc) used in the present apparatus and methods. The electronics include appropriate AC-to-DC power supply for the apparatus.

In one embodiment the microprocessor is a 16-bit type; however, a 32-bit version may also be used. This microprocessor is supported with flash re-programmable memory as well as static RAM (random access memory). Most contemporary microprocessors incorporate one or more on-chip serial I/O interfaces. In this design, this interface is used as a diagnostic port for the apparatus, to gain direct access to the microprocessor and hardware subsystems for maintenance and trouble-shooting purposes. Other on-chip I/O interfaces connect directly to a user control panel equipped with control pushbuttons and status indicators.

The microprocessor and core set of I/O interface electronics may also include a bar-code reader to permit the user to identify each substrate by its attached bar-code number. This may be interpreted by the apparatus to select a particular protocol for the processing steps in the chemical reactions such as, for example, a wash and dry protocol and the like, compatible with the substrate type and experiment plan. The I/O interface electronics may also incorporate a 10-BaseT LAN (Local Area Network) interface for communication to other computer systems, file servers and information resources. The I/O interface electronics may incorporate signal conditioning and A-to-D circuitry to convert and interpret flow, fluid-level, mechanical position, temperature and gas pressure sensors. These signals are input to the microprocessor for analysis and interpretation by the embedded real-time control software. Finally, this core set of electronics may include digital I/O circuitry to control the flow and routing of reagents and gases via electronically actuated valves. These digital I/O interfaces may also control fluid reagent pre-heater and pre-cooler units.

A small set of I/O interfaces may interact directly with a flow device of the invention. As stated above, the process throughput of the apparatus can be increased by adding multiple flow devices. Each such flow device requires added I/O interfaces. The flow device I/O interfaces control the substrate elevator motor, flow device tilt motor, fluid, vapor and gas valves, re-circulation/drain pump and heat-exchanger heater/cooler units. The microprocessor and all of the control electronics are powered by an AC-to-DC converting power supply incorporated as part of the apparatus. Accordingly, the apparatus of the invention supports multiple flow devices and their concurrent operation.

Embodiments of the invention will be discussed next in more detail, by way of illustration and not limitation, with reference to the accompanying figures. As a general note, figures may not be to scale and some elements of the figures may be accentuated for purposes of illustration.

A particular example of a flow device in accordance with the present invention is depicted in FIGS. 1-4. Flow device 100 comprises housing 101 with front wall 102, rear wall 104, sidewalls 106 and 108 and top and bottom walls 110 and 112. The interior of housing 101 comprises housing chamber 114. Inlets 116, 118, 120 and 122 are disposed in sidewalls 106 (116 and 118) and 108 (120 and 122), respectively, and are in fluid communication with housing chamber 114. As can be seen in FIG. 1, inlets 116 and 120 comprise angled channels 124 and 126, respectively. These angled channels are provided to assist the contact between entering fluid reagents and the surface of the substrate. The angle 124A and 126A of channels 124 and 126, respectively, from the horizontal, or from a line parallel to top wall 110, is about 3 to about 15 degrees, usually, about 5 to about 10 degrees. Housing chamber 114 comprises shaft 128, which is in fluid communication with the remainder of housing chamber 114.

Flow device 100 is sectioned along lines A-A as illustrated in FIG. 3 and approximately along lines B-B as illustrated in FIG. 2. Cap 146 comprises cap body 148 and inlet 150. Cap 146 fits onto housing 10. The beveled under-portion of body 148 interlocks into the beveled top of housing 101. The top is held in place by pins, clamps, springs, friction-fit as described previously. Cap 146 prevents dust and debris from entering the housing chamber 114 during processing. Cap 146 is placed or removed as needed to access housing chamber. When cap 146 is in place, inlet 150 may be employed to introduce a gas into housing chamber 114. As mentioned above, the gas may assist in the maintaining of a fluid film without droplet formation on the surface of substrate 140. Following the drying process step, gas introduced via inlet 150, may serve to exclude atmospheric gas from the housing chamber thereby protecting the substrate from oxygen degradation.

FIG. 4 depicts a magnetic lifter 130 with integral finger 132 is movable within shaft 128. Magnetic lifter 130 has outer plastic coating 134 and inner magnet 136. Outlet 138 is disposed in bottom wall 112 of housing 101. Substrate 140 is within the interior of housing chamber 114 and is supported therein by finger 132. Substrate represents a single oligonucleotide support substrate. Substrate 140 is movable in and out of housing chamber 114 and is guided by guideposts 142. Front wall 102 is secured to rear wall 104 of housing 101 by means of screws 144. External to device 100 is magnetically responsive pellet 137, which is movably mounted and moved by an appropriate motor (not shown) in direction of travel 137a.

Figure 8:
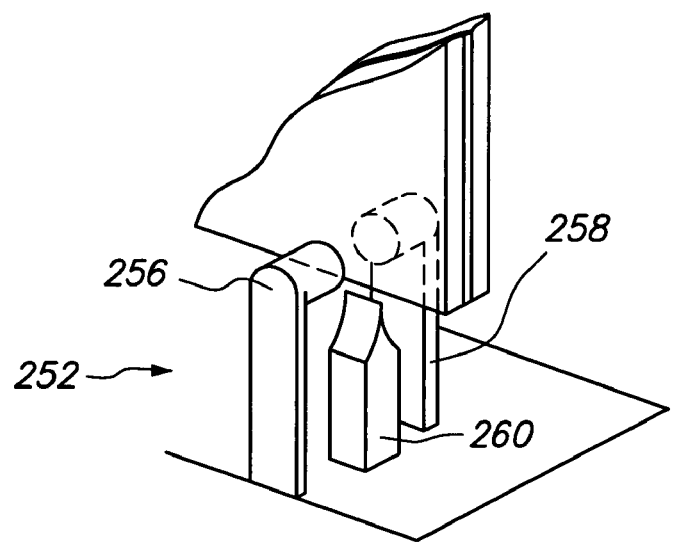
FIG. 8 is a partial view in perspective depicting a separator mechanism of the device of FIG. 6.

Another particular example of a flow device in accordance with the present invention is depicted in FIGS. 6-8. Flow device 200 comprises housing 201 with front wall 202, rear wall 204, sidewalls 206 and 208 and top and bottom walls 210 and 212. The interior of housing 201 comprises housing chamber 214. Inlets 216, 218, 220 and 222 are disposed in sidewalls 206 (216 and 218) and 208 (220 and 222), respectively, and are in fluid communication with housing chamber 214.

As can be seen in FIG. 6, inlets 216 and 220 comprise angled channels 224 and 226, respectively. These angled channels are similar to those in flow device 100 of FIGS. 1-4. Housing chamber 214 comprises shaft 228, which is in fluid communication with the remainder of housing chamber 214. Magnetic lifter 230 with integral finger 232 is movable within shaft 228. Magnetic lifter 230 has a design substantially the same as magnetic lifter 130 of FIGS. 1-4. Outlet 238 is disposed in bottom wall 212 of housing 201.

Flow device 200 is sectioned along lines A-A as illustrated in FIG. 5A and approximately along lines B-B as illustrated in FIG. 5B. Substrate 240 is within the interior of housing chamber 214 and is supported therein by finger 232. Substrate 240 represents a sandwich comprising a backing, an oligonucleotide support substrate and interposed sealing gasket. Such a sandwich is disclosed separately in Agilent Technologies Inc U.S. patent application Ser. Nos. 10/172,850 "Form in Place Gaskets for Assays" filed Jun. 14, 2002; Ser. No. 10/172,892 "Improved Hybridization Process for Arrays" filed Jun. 14, 2002; and Ser. No. 10/173,292 "Multiple Arrays Format" filed Jun. 14, 2002, the relevant disclosures of which are incorporated herein by reference. Substrate sandwich 240 is movable in and out of housing chamber 214 and is guided by biasing members 242. FIG. 7 depicts biasing member 242. Biasing member 242 comprises two flexible portions 242a and 242b with center portion 243 with a hole 243a corresponding to an inlet in the housing wall as shown in FIG. 6. Ends 245 of biasing member 242 are cylindrical and engage an edge of substrate 240. When substrate sandwich 240 is fully lowered into housing chamber 214, separators 262 and 264 guide the substrate and position it so that wedge member 260 separates the backing from support substrate. This occurs only when the sandwich 240 is fully submerged. Separating substrate sandwich 240 exposes the oligonucleotide-supporting surface of the substrate to the desired processing reagents. Separators 262 and 264 of a design similar to that for separators 252 and 254 are shown in FIG. 8. Separator 252 is shown and comprises biasing members 256 and 258 as well as wedge member 260.

Front wall 202 is secured to rear wall 204 of housing 201 by means of screws 244. Magnetic lifter 230 is moved by means of a magnetically responsive pellet 237 and motor mechanism (not shown) in a manner similar to that for device 100 of FIGS. 1-4. Also depicted in FIG. 6 is cap 246 for the top of housing 201. Cap 246 comprises cap body 248 and inlet 250. Separators 252 and 254 project downwardly from the underside of cap body 248. In practice, when cap 246 is fully lowered into housing chamber 214, separators 252 and 254 guide the substrate sandwich 240 and position it so that wedge member 260 separates the backing from support substrate. The design of separators 252 and 254 may be seen with reference to FIG. 8. Cap 246 has angled portions 266 protruding from the underside of cap body 248. The top of housing 201 comprises angled corners 268 and 270, which permit protruding portion 266 of cap body 248 to be smoothly engaged. When cap 246 is in place, inlet 250 may be employed to introduce a gas into housing chamber 214. As mentioned above, the gas may assist in the maintaining of a fluid film without droplet formation on the surface of substrate 240. Following the drying process step, gas introduced via inlet 250 may serve to exclude atmospheric gas from the housing chamber thereby protecting the substrate from oxygen degradation.

Figure 9:
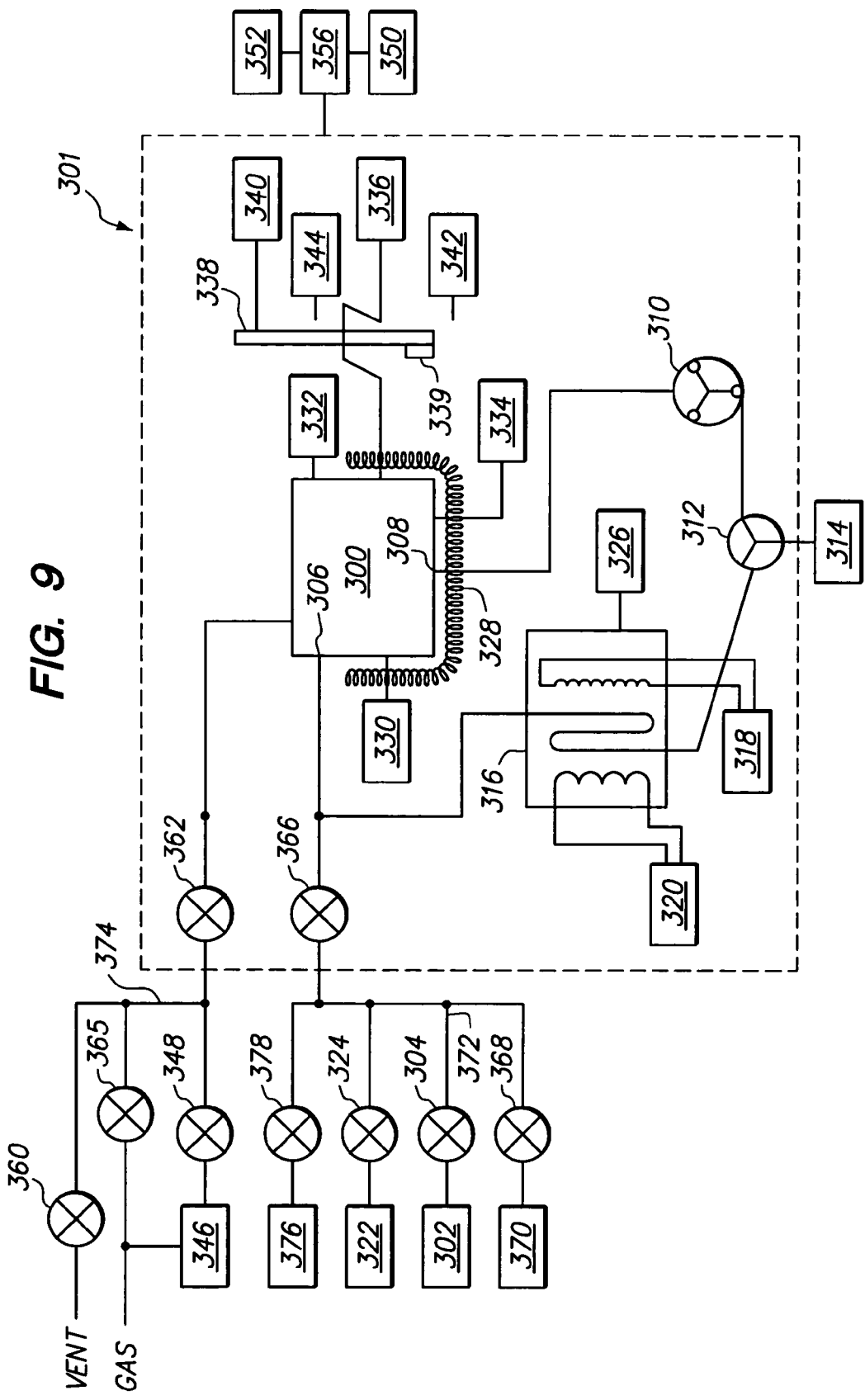
FIG. 9 is a schematic diagram depicting an apparatus of the invention.

An example of an apparatus 301 in accordance with the present invention is shown in FIG. 9. Flow device 300, which may be the same as or similar to those described above in FIGS. 1 and 6, is in fluid communication with four fluid reagent sources 302, 322, 370 and 376. Valve 304 controls the input of fluid reagent from source 302 into flow device 300 through inlet 306 via fluid manifold 372 and valve 366. Similarly, valve 324 controls the input of fluid reagent from source 322, valve 368 controls the input of fluid reagent from source 370 and valve 378 controls the input of fluid reagent from source 376. Outlet 308 is in fluid communication with pump 310, which controls the flow of fluid reagents exiting from flow device 300 as well as circulation of fluid reagents within flow device 300. Pump 310 is in fluid communication with two-way valve 312, which controls the flow of fluid reagent to waste reservoir 314 or to recirculate to flow device 300. Recirculated fluid reagent passes through heat exchanger 316 where fluid reagent is either heated by means of heater unit 318 or cooled by means of cooling unit 320. The temperature of the fluid reagent is monitored by temperature sensor 326 associated with heat exchanger 316.

Flow device 300 is surrounded by thermal jacket 328 and the temperature of flow device 300 is monitored by temperature sensor 330. The level of fluid reagent in flow device 300 is monitored by means of full sensor 332 and empty sensor 334. The orientation of flow device 300 is controlled by tilt mechanism 336. Also shown is a part 338 of an elevator mechanism for lifting a substrate inside flow device 300. Part 338 comprises magnet 339 moved by actuator 340. Also shown are wash position sensor 342 and load/unload position sensor 344. Solvent vapor source 346 is controlled by valve 348. Valves 360 and 365 control other vent and gas sources, respectively. All three sources are in fluid communication with flow device 300 via gas manifold 374 and valve 362.

Apparatus 301 also comprises hybridization station 350 and transfer mechanism 352. The operations of apparatus 301 are controlled by computer 356, which controls the functions of flow device 300 and its accompanying valves, pumps, sensors, heat exchanger, etc., hybridization station 350 and transfer mechanism 352 consistent with the methods of the present invention.

Figure 10:
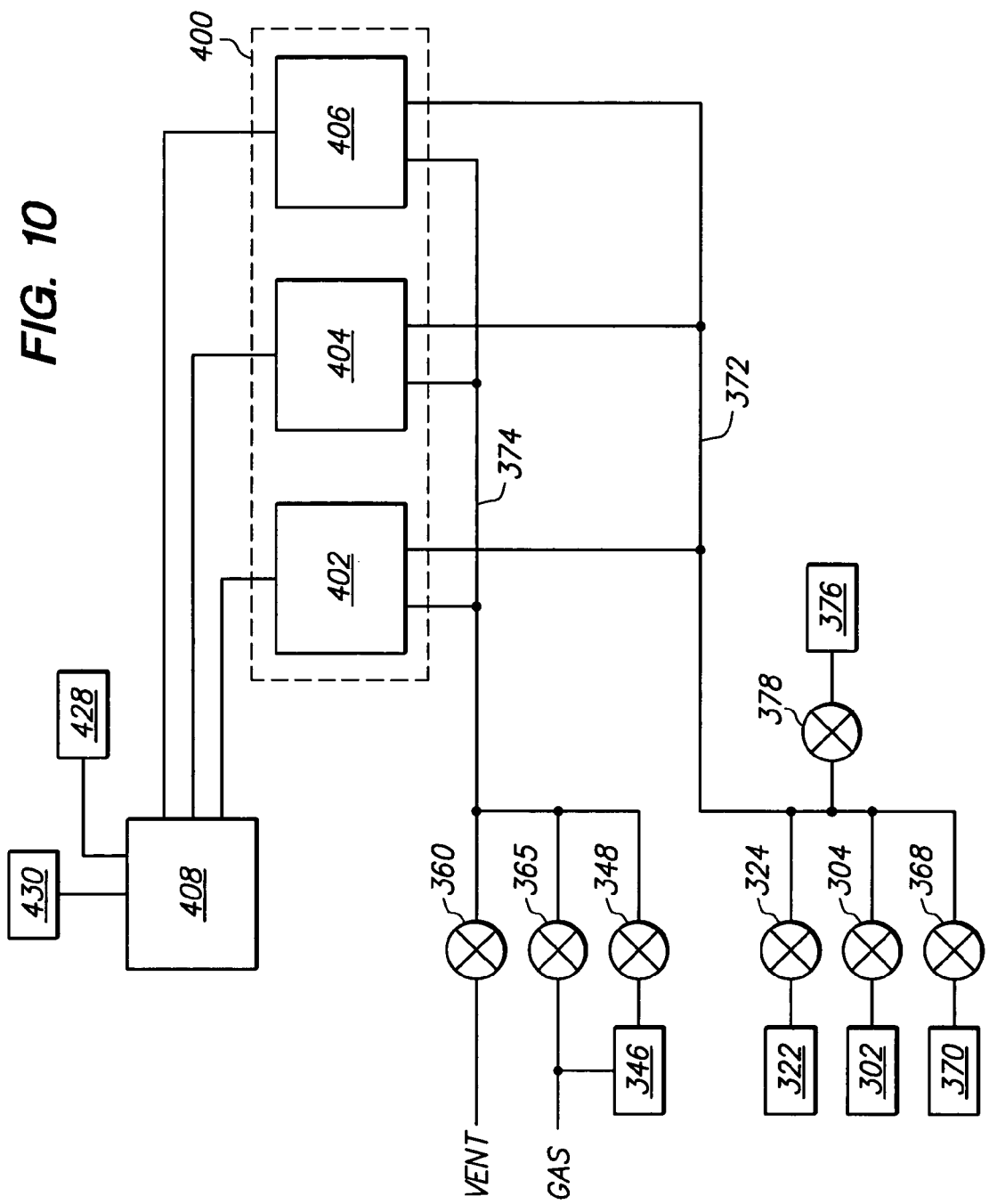
FIG. 10 is a schematic diagram depicting an alternate embodiment of an apparatus of the invention.

Apparatus 400 is depicted in FIG. 10 and comprises three flow devices (402, 404 and 406) in accordance with the present invention. Computer 408 controls the operations of each of the flow devices. Each of the flow devices is in fluid communication with three fluid reagent reservoirs, 322, 302, 370, 376 by means of manifold 372 Each of the flow devices is in fluid communication with solvent vapor source 346, vent and gas sources via manifold 374. Computer 408 also controls the functions of hybridization station 428 and transfer mechanism 430.

The aforementioned apparatus may be employed in methods for conducting chemical reactions. The chemical reaction can be any chemical reaction that involves chemical reactants in solution and chemical reactants associated with the surface of a substrate or a support. The reactions may involve covalent or non-covalent binding. The chemical reactions may be, for example, reactions between members of a specific binding pair, condensation reactions, oxidation reactions, reduction reactions, displacement reactions, and so forth. A step in a chemical reaction refers to any step that is associated with a particular chemical reaction and includes the chemical reaction itself, processing steps such as washing, drying and the like, e.g., washing and drying of substrate surfaces, and so forth.

The invention has particular application to binding reactions between members of a specific binding pair. A member of a specific binding pair ("sbp member") is one of two different molecules, having an area on the surface or in a cavity, which specifically binds to and is thereby defined as complementary with a particular spatial and polar organization of the other molecule. The members of the specific binding pair include ligand and receptor (antiligand). Specific binding pairs include members of an immunological pair such as antigen-antibody, biotin-avidin, hormones-hormone receptors, nucleic acid duplexes, IgG-protein A, polynucleotide pairs such as DNA-DNA, DNA-RNA, and the like.

As mentioned above, hybridization reactions between surface-bound probes and target molecules in solution may be used to detect the presence of particular biopolymers. Hybridization involves members of a specific binding pair that comprises polynucleotides. Hybridization is based on complementary base pairing. When complementary single stranded nucleic acids are incubated together, the complementary base sequences pair to form double stranded hybrid molecules. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present.

In the methods of the invention, one or more liquid samples are contacted with the surface of the substrate that comprises the chemical compounds. Contact may be achieved by methods well known in the art such as, for example, drop wise application of sample to individual features on the surface of the substrate, irrigation of the substrate surface with a solution containing the sample, immersion of the substrate in a solution containing the sample, mating of the surface of the substrate with a porous member containing the sample and so forth. The sample may be a trial sample, a reference sample, a combination of the foregoing, or a known mixture of components such as polynucleotides, proteins, polysaccharides and the like (in which case the arrays may be composed of features that are unknown such as polynucleotide sequences to be evaluated). The samples may be from biological assays such as in the identification of drug targets, single-nucleotide polymorphism mapping, monitoring samples from patients to track their response to treatment and/or assess the efficacy of new treatments, and so forth. For hybridization reactions the sample generally comprises a target molecule that may or may not hybridize to a surface-bound molecular probe. The term "target molecule" refers to a known or unknown molecule in a sample, which will hybridize to a molecular probe on a substrate surface if the target molecule and the molecular probe contain complementary regions. In general, the target molecule is a "biopolymer," i.e., an oligomer or polymer. The present devices and methods have particular application to various processing steps involved with the aforementioned hybridization reactions.

An oligomer or polymer is a chemical entity that contains a plurality of monomers. It is generally accepted that the term "oligomers" is used to refer to a species of polymers. Examples of polymers include polydeoxyribonucleotides, polyribonucleotides, other polynucleotides that are C-glycosides of a purine or pyrimidine base, or other modified polynucleotides, polypeptides, polysaccharides, and other chemical entities that contain repeating units of like chemical structure. Exemplary of oligomers are oligonucleotides and peptides.

A biomonomer refers to a single unit, which can be linked with the same or other biomonomers to form a biopolymer (for example, a single amino acid or nucleotide with two linking groups one or both of which may have removable protecting groups). A biomonomer fluid or biopolymer fluid refer to a liquid containing either a biomonomer or biopolymer, respectively (typically in solution).

A biopolymer is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

Polynucleotides are compounds or compositions that are polymeric nucleotides or nucleic acid polymers. The polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The polynucleotides include nucleic acids, and fragments thereof, from any source in purified or unpurified form including DNA (dsDNA and ssDNA) and RNA, including tRNA, mRNA, rRNA, cDNA, mitochondrial DNA and RNA, chloroplast DNA and RNA, DNA/RNA hybrids, or mixtures thereof, genes, oncogenes, chromosomes, plasmids, cosmids, the genomes of biological material such as microorganisms, e.g., bacteria, yeasts, phage, chromosomes, viruses, viroids, molds, fungi, plants, animals, humans, and the like. The polynucleotide can be only aminor fraction of a complex mixture such as a biological sample.

A nucleotide refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

The substrate to which a plurality of chemical compounds is attached is usually a porous or non-porous water insoluble material. The substrate can have any one of a number of shapes such as strip, plate, disk; rod; particle, and the like. The substrate can be hydrophilic or capable of being rendered or rendered hydrophilic or it may be hydrophobic. The substrate may be glass such as flat glass whose surface has been chemically activated to substrate binding or synthesis thereon, glass available as Bioglass and the like. However, the substrate may be made from other materials such as, e.g., plastic, metal and the like. The surface of the substrate, which comprises the chemical compounds, may be smooth or substantially planar, or have irregularities, such as depressions or elevations.

The surface of a substrate is normally treated to create a primed or functionalized surface. By the term "functionalized surface" is meant a substrate surface that has been modified so that a plurality of functional groups are present thereon usually at discrete sites on the surface. In one embodiment, the surface of the substrate, such as a glass substrate, is siliceous, i.e., comprises silicon oxide groups, either present in the natural state, e.g., glass, silica, silicon with an oxide layer, etc., or introduced by techniques well known in the art. Another method for attachment is described in U.S. Pat. No. 6,219,674 (Fulcrand, et al.). Another method for attachment is described in U.S. Pat. No. 6,258,454 (Lefkowitz, et al.). A procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to carry out the present methods. Such a derivatization procedure is described in EP 0 173 356 B1, the relevant portions of which are incorporated herein by reference. Other methods for treating the surface of a substrate will be suggested to those skilled in the art in view of the teaching herein.

The apparatus and methods of the present invention are particularly useful with substrates comprising an array or a plurality of arrays arranged on the surface of the substrate. An array includes any one, two- or three-dimensional arrangement of addressable regions bearing a particular biopolymer such as polynucleotides, associated with that region. An array is addressable in that it has multiple regions of different moieties, for example, different polynucleotide sequences, such that a region or feature or spot of the array at a particular predetermined location or address on the array can detect a particular target molecule or class of target molecules although a feature may incidentally detect non-target molecules of that feature. The one or more arrays disposed along a surface of the support are usually separated by inter-array areas. Normally, the surface of the support opposite the surface with the arrays does not carry any arrays.

The surface of the substrate may carry at least one, two, four, ten, up to thousands of arrays, usually chemical arrays, i.e., arrays of chemical compounds. Depending upon intended use, any or all of the arrays may be the same or different from one another and each may contain multiple spots or features of chemical compounds such as, e.g., biopolymers in the form of polynucleotides or other biopolymer. A typical array may contain more than ten, more than one hundred, more than one thousand, more than ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges.

Each feature, or element, within the molecular array is defined to be a small, regularly shaped region of the surface of the substrate. The features are arranged in a predetermined manner. Each feature of an array usually carries a predetermined chemical compound or mixtures thereof. Each feature within the molecular array may contain a different molecular species, and the molecular species within a given feature may differ from the molecular species within the remaining features of the molecular array. Some or all of the features may be of different compositions. Each array may contain multiple spots or features and each array may be separated by spaces or areas. It will also be appreciated that there need not be any space separating arrays from one another. Interarray areas and interfeature areas are usually present but are not essential. These areas do not carry any chemical compound such as polynucleotide (or other biopolymer of a type of which the features are composed). Interarray areas and interfeature areas typically will be present where arrays are formed by the conventional in situ process or by deposition of previously obtained moieties. In one approach, arrays are synthesized by depositing for each feature at least one droplet of reagent such as from a pulse jet (for example, an inkjet type head) but may not be present when, for example, photolithographic array fabrication processes are used. It will be appreciated though, that the interarray areas and interfeature areas, when present, could be of various sizes and configurations.

Biopolymer arrays can be fabricated by depositing previously obtained biopolymers (such as from synthesis or natural sources) onto a substrate, or by in situ synthesis methods. Methods of depositing obtained biopolymers include dispensing droplets to a substrate from dispensers such as pin or capillaries (such as described in U.S. Pat. No. 5,807,522) or such as pulse jets (such as a piezoelectric inkjet head, as described in PCT publications WO 95/25116 and WO 98/41531, and elsewhere). For in situ fabrication methods, multiple different reagent droplets are deposited from drop dispensers at a given target location in order to form the final feature (hence a probe of the feature is synthesized on the array substrate). The in situ fabrication methods include those described in U.S. Pat. No. 5,449,754 for synthesizing peptide arrays, and described in WO 98/41531 and the references cited therein for polynucleotides.

The chemistry of the synthesis of polynucleotides is described in detail, for example, in Caruthers, *Science* 230: 281-285, 1985; Itakura, et al., *Ann. Rev. Biochem.* 53: 323-356; Hunkapillar, et al., *Nature* 310: 105-110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, and 5,869,643, EP 0294196, and elsewhere.

The devices, apparatus and methods of the present invention are particularly useful with substrates comprising oligonucleotide arrays and polynucleotide arrays for determinations of polynucleotides. As explained briefly above, in the field of bioscience, arrays of oligonucleotide or polynucleotide probes, fabricated or deposited on a surface of a substrate, are used to identify DNA sequences in cell matter. The arrays generally involve a surface containing a mosaic of different oligonucleotides or sample nucleic acid sequences or polynucleotides that are individually localized to discrete, known areas of the surface. In one approach, multiple identical arrays across a complete front surface of a single substrate or support are used. However, one or more of the arrays may be different from the other arrays on the substrate surface. Ordered arrays containing a large number of oligonucleotides have been developed as tools for high throughput analyses of genotype and gene expression. Oligonucleotides on a solid support surface recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

Oligonucleotides are polynucleotides, usually single stranded, either synthetic or naturally occurring. The length of an oligonucleotide is generally governed by the particular role thereof, such as, for example, probe, primer and the like. Oligonucleotide probes are oligonucleotides employed to bind to a portion of a polynucleotide such as another oligonucleotide or a target polynucleotide sequence. Usually, the oligonucleotide probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The design, including the length, and the preparation of the oligonucleotide probes are generally dependent upon the sequence to which they bind. Usually, the oligonucleotide probes are at least about 2 nucleotides, preferably, about 5 to about 100 nucleotides, more preferably, about 10 to about 50 nucleotides, and usually, about 15 to about 30 nucleotides, in length.

Various ways may be employed to produce an array of polynucleotides on supports or surfaces such as glass, metal, plastic and the like. Such methods are known in the art. One such method is involves known solid phase chemistry, photolabile protecting groups and photolithography methods. Binary masking techniques are employed in one embodiment of the above. Arrays can be fabricated using drop deposition from pulse jets of either polynucleotide precursor units (such as monomers) in the case of in situ fabrication, or the previously obtained polynucleotide. Such methods are described in detail in, for example, U.S. Pat. Nos. 6,242,266, 6,232,072, 6,180,351, 6,171,797 and 6,323,043, U.S. patent application Ser. No. 09/302,898 filed Apr. 30, 1999, by Caren, et al., and the references cited therein.

Another in situ method employs inkjet printing technology to dispense the appropriate phosphoramidite reagents and other reagents onto individual sites on a surface of a support. Oligonucleotides are synthesized on a surface of a substrate in situ using phosphoramidite chemistry. For example, see U.S. Pat. No. 5,700,637 and PCT WO 95/25116 and PCT application WO 89/10977. Other methods for synthesizing arrays of oligonucleotides on a surface include those disclosed by Gamble, et al., WO97/44134; Gamble, et al., WO98/10858; Baldeschwieler, et al., WO95/25116; Brown, et al., U.S. Pat. No. 5,807,522; and the like.

Figure 11:
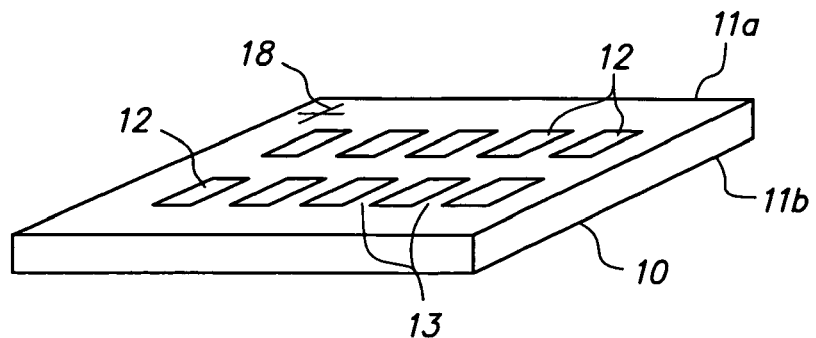
FIG. 11 is a perspective view of a substrate bearing multiple arrays.
Figure 12:
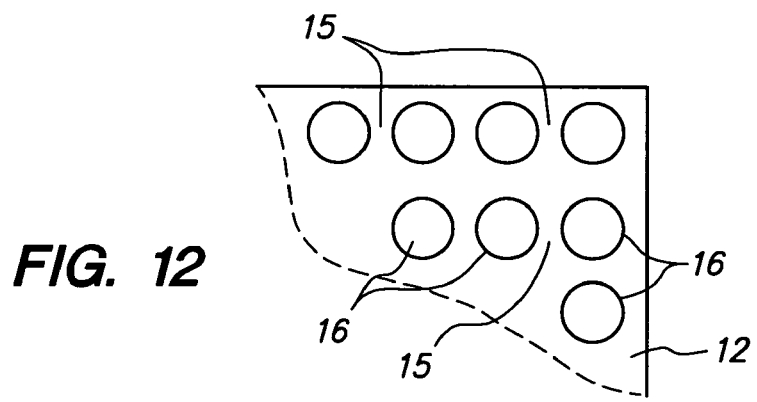
FIG. 12 is an enlarged view of a portion of FIG. 11 showing some of the identifiable individual regions (or "features") of a single array of FIG. 11.
Figure 13:
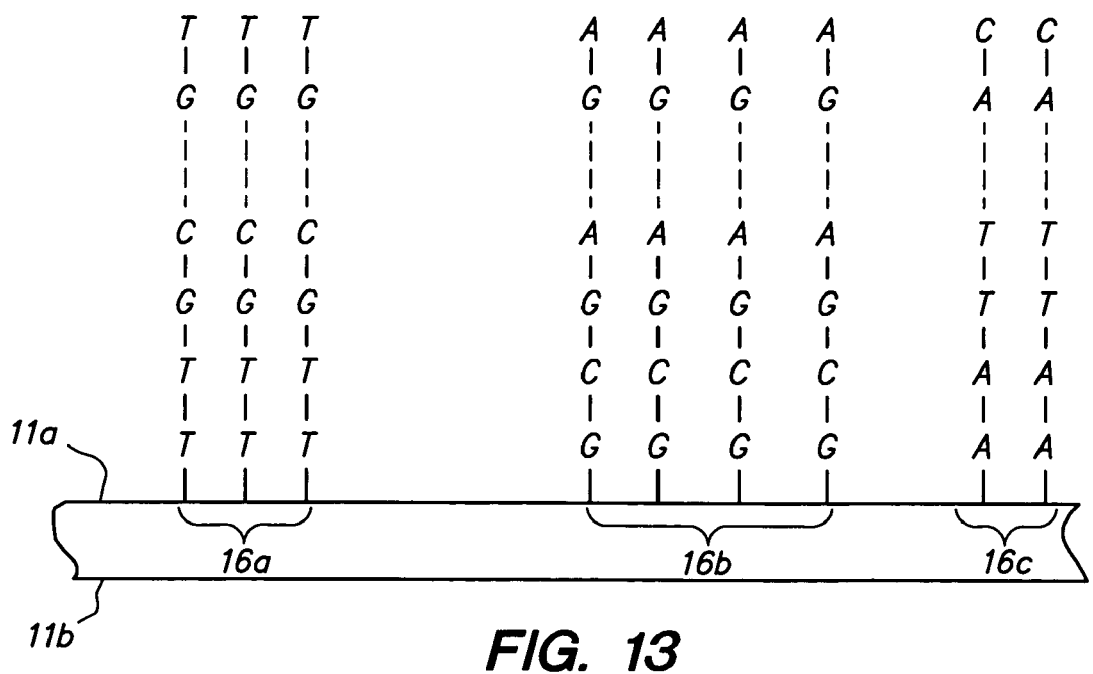
FIG. 13 is an enlarged cross-section of a portion of FIG. 12.

Referring to FIGS. 11-13, there is shown multiple identical arrays 12 (only some of which are shown in FIG. 11), separated by inter-array regions 13, across the complete front surface 11a of a single transparent substrate 10. However, the arrays 12 on a given substrate need not be identical and some or all could be different. Each array 12 will contain multiple spots or features 16 separated by inter-feature regions 15. A typical array 12 may contain from 100 to 100,000 features. All of the features 16 may be different, or some or all could be the same. Each feature carries a predetermined moiety (such as a particular polynucleotide sequence), or a predetermined mixture of moieties (such as a mixture of particular polynucleotides). This is illustrated schematically in FIG. 13 where different regions 16 are shown as carrying different polynucleotide sequences.

An oligonucleotide probe may be, or may be capable of being, labeled with a reporter group, which generates a signal, or may be, or may be capable of becoming, bound to a support. Detection of signal depends upon the nature of the label or reporter group. Commonly, binding of an oligonucleotide probe to a target polynucleotide sequence is detected by means of a label incorporated into the target. Alternatively, the target polynucleotide sequence may be unlabeled and a second oligonucleotide probe may be labeled. Binding can be detected by separating the bound second oligonucleotide probe or target polynucleotide from the free second oligonucleotide probe or target polynucleotide and detecting the label. In one approach, a sandwich is formed comprised of one oligonucleotide probe, which may be labeled, the target polynucleotide and an oligonucleotide probe that is or can become bound to a surface of a support. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target polynucleotide, allowing the target polynucleotide to hybridize to a surface-bound oligonucleotide probe, washing away the unbound target polynucleotide and detecting the labeled target polynucleotide that remains. Direct detection of labeled target polynucleotide hybridized to surface-bound oligonucleotide probes is particularly advantageous in the use of ordered arrays.

In one approach, cell matter is lysed, to release its DNA as fragments, which are then separated out by electrophoresis or other means, and then tagged with a fluorescent or other label. The DNA mix is exposed to an array of oligonucleotide probes, whereupon selective attachment to matching probe sites takes place. The array is then washed and the result of exposure to the array is determined. In this particular example, the array is imaged by scanning the surface of the support so as to reveal for analysis and interpretation the sites where attachment occurred.

The signal referred to above may arise from any moiety that may be incorporated into a molecule such as an oligonucleotide probe for the purpose of detection. Often, a label is employed, which may be a member of a signal producing system. The label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth. The reporter molecule can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like.

The signal may be produced by a signal producing system, which is a system that generates a signal that relates to the presence or amount of a target polynucleotide in a medium. The signal producing system may have one or more components, at least one component being the label. The signal producing system includes all of the reagents required to produce a measurable signal. The signal producing system provides a signal detectable by external means, by use of electromagnetic radiation, desirably by visual examination. Signal-producing systems that may be employed in the present invention are those described more fully in U.S. Pat. Nos. 6,558,908, 6,251,588, 6,235,483 and 6,132,997, the relevant disclosure of which is incorporated herein by reference.

The arrays and the liquid samples in the wells are maintained in contact for a period of time sufficient for the desired chemical reaction to occur. The conditions for a reaction, such as, for example, period of time of contact, temperature, pH, salt concentration and so forth, are dependent on the nature of the chemical reaction, the nature of the chemical reactants including the liquid samples, and the like. The conditions for binding of members of specific binding pairs are generally well known and will not be discussed in detail here. The conditions for the various processing steps are also known in the art.

As mentioned above, the present apparatus and methods are particularly suitable for conducting hybridization reactions. Such reactions are carried out on a substrate or support comprising a plurality of features relating to the hybridization reactions. The substrate is exposed to liquid samples and to other reagents for carrying out the hybridization reactions. The support surface exposed to the sample is incubated under conditions suitable for hybridization reactions to occur. As mentioned above, in some instances a cover slide is placed over the surface of the substrate on which chemical reactions are to be carried out, thus, forming a sandwich. When this substrate-cover slide sandwich is inserted into the present flow device, a separator assists in separating the substrate and the cover slide so that fluid reagents may contact the surface of the substrate on which the chemical reactions, including processing steps, are to occur.

After the appropriate period of time of contact between the liquid samples in the wells and the arrays on the surface of the substrate, the contact is discontinued and various processing steps are performed. The amount of the fluid reagents employed in each processing step in the method of the present invention is dependent on the nature of the reagents and the size of the housing chamber. Such amounts should be readily apparent to those skilled in the art in view of the disclosure herein. Typically, the amounts of the fluid reagents are those necessary to successfully accomplish the particular processing step. The time period for contact of the fluid reagents and the substrate is dependent upon the specific reaction and fluid reagents being utilized.

Following the processing of the substrate, it is moved to an examining device where the surface of the substrate on which the arrays are disposed is interrogated. The examining device may be a scanning device involving an optical system.

Reading of the array may be accomplished by illuminating the array and reading the location and intensity of resulting fluorescence at each feature of the array. For example, a scanner may be used for this purpose where the scanner may be similar to, for example, the AGILENT Microarray Scanner available from Agilent Technologies Inc, Palo Alto, Calif. Other suitable apparatus and methods are described in U.S. patent applications: Ser. No. 09/846,125 "Reading Multi-Featured Arrays" by Dorsel, et al.; and Ser. No. 09/430,214 "Interrogating Multi-Featured Arrays" by Dorsel, et al. The relevant portions of these references are incorporated herein by reference. However, arrays may be read by methods or apparatus other than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature that is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

In another particular embodiment, the method is carried out under computer control, that is, with the aid of a computer. For example, an IBM® compatible personal computer (PC) or more usually, an embedded digital microprocessor may be utilized. The computer is driven by software specific to the methods described herein. The preferred computer hardware capable of assisting in the operation of the methods in accordance with the present invention involves a system with at least the following specifications: processor with 16-bit word length or better capable of executing more than 1 million instructions per second, at least 16 megabytes of random access memory (RAM) and at least 16 megabytes of read only memory (ROM), running under any real time operating system, or for a PC Windows 95, Windows 2000, Windows NT 4.0, or Linux operating systems (or successors thereof).

Examples of software or computer programs used in assisting in conducting the present methods may be written in any language capable of handling hardware interrupts and real time control, preferably, in BASIC, Visual BASIC, JAVA, assembly language, C, Visual C or C++, as exemplified below in the Examples. It should be understood that the above computer information and the software used herein are by way of example and not limitation. The present methods may be adapted to other computers and software.

As indicated above, a computer program may be utilized to carry out the above method steps. For example, in one embodiment a computer program provides for (a) inserting a substrate into a housing chamber of a device as described above, (b) introducing a fluid reagent for performing the step into the housing chamber by means of the inlet, and (c) removing the fluid reagent from the housing chamber by means of the outlet in a controlled manner at a rate that substantially eliminates droplet formation of the fluid on the surface of the substrate resulting in a substantially dry surface.

In another embodiment the computer program provides for (1) removing a support substrate from a hybridization chamber; (2) loading the substrate into the flow device of this invention; (3) flooding the flow device with disassembly buffer (i.e. wash buffer); (4) diluting and washing away the hybridization buffer with excess un-bound target material; (5) replacing the disassembly buffer with the first of one or more wash buffers by simultaneous draining and filling of the flow device of the invention; (6) washing the substrate for a period of time; (7) replacing the wash buffer with a subsequent wash buffer by simultaneous draining and filling of the flow device; and (8) following the last wash, drying the substrate by a method suited to its hydrophobic or hydrophilic surface properties.

Another aspect of the present invention is a computer program product comprising a computer readable storage medium having a computer program stored thereon which, when loaded into a computer, performs the aforementioned method.

One aspect of the invention is the product of the above method, namely, the assay result, which may be evaluated at the site of the testing or it may be shipped to another site for evaluation and communication to an interested party at a remote location if desired. By the term "remote location" is meant a location that is physically different than that at which the results are obtained. Accordingly, the results may be sent to a different room, a different building, a different part of city, a different city, and so forth. Usually, the remote location is at least about one mile, usually, at least ten miles, more usually about a hundred miles, or more from the location at which the results are obtained. The data may be transmitted by standard means such as, e.g., facsimile, mail, overnight delivery, e-mail, voice mail, and the like.

"Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

The present invention addresses many of the limitations of the known methods and apparatus. The present invention provides consistent substrate processing through mechanized washing and drying. Computer control of process step initiation, timing durations and temperatures is superior to manual processing methods. This invention subjects each support substrate to the same process conditions, whether it is the first or last of a batch of substrates. Mechanically washed and dried microarray support substrates perform better than those processed manually, exhibiting improved spatial uniform, sometimes lower and more uniform background levels, improved signal to background ratios, improved substrate-to-substrate expression consistency.

Certain embodiments of the present invention provides reduction of cross-contamination and degradation of wash reagents. Automatic replenishment of wash reagents during processing reduces the probability of cross-contamination and eliminates reagent degradation due to repetitive re-use when processing large batches of substrates. Fresh reagents are drawn from the appropriate reservoirs at the start of each process step eliminating the inconvenience and variability of manually refreshing pre-heated or pre-cooled reagents.

A flexible wash and dry protocol is provided by certain embodiments and is applicable to hydrophobic and hydrophilic support substrate surfaces. It is capable of supporting the multiple washing and drying protocols needed by different microarray platform chemistries such as, for example, in situ synthesized microarrays, whole oligonucleotide and cDNA deposition microarrays.

Certain embodiments of the present invention support any size or number of patterned regions per substrate. A moderate volume flow chamber encloses the microarray support substrate during processing ensuring that the entire substrate surface is processed uniformly independent of the number of patterned regions per substrate.

Certain embodiments of the present invention eliminate the need to handle the substrate between the time it is removed from the incubator and loaded into the process flow device and the time that the substrate is dry and ready for scanning. Certain embodiments of the present invention incorporate automatic loading and unloading mechanisms that submerge the substrate in wash buffer and retrieve it, ensuring that the laboratory worker's hands and gloves remain dry.

In certain embodiments of the present invention the microarray substrate is not exposed to the ambient atmosphere when wet. Simultaneous filling and draining of the flow device in the method of the invention reduces or eliminates exposure of the substrates to air between processing steps such as, e.g., wash steps. Certain embodiments of the present invention, by virtue of flow device design and fluid controls, maintain the support substrate in a constant liquid fluid environment until it is intentionally dried. This is an improvement over the use of multiple dunk-tanks for each process step. In certain embodiments of this invention, all process-step to process-step transitions are made in fluid and, thus, the surface of the substrate is maintained wet during the removal of the hybridization buffer together with excess unbound target material—(1) the support substrate is removed from the incubator as a sealed hybridization chamber containing hybridization buffer (for example, as a hybridization chamber formed by using silicone gaskets on glass as disclosed in U.S. patent application Ser. No.: 10/172,850 "Form in Place Gaskets for Assays" filed Jun. 14, 2002; Ser. No. 10/172,892 "Improved Hybridization Process for Arrays" filed Jun. 14, 2002; and Ser. No. 10/173,292 "Multiple Arrays Format" filed Jun. 14, 2002, the relevant disclosures of which are incorporated herein by reference; (2) the substrate is loaded into the flow device of this invention; (3) the flow device is flooded with disassembly buffer and the hybridization chamber is unsealed; (4) the hybridization buffer with excess un-bound target material is diluted and washed away thereby removing substantially all of the hybridization buffer prior to the contact of the substrate surface with a first wash buffer (substantially all of the hybridization buffer means at least 90%, at least 91%, at least 92%, at least 93%, at least 94%, at least 95%, at least 96%, at least 97%, at least 98%, at least 99%, at least 99.5%, at least 99.9%, 100%; (5) the disassembly buffer is replaced with the first of one or more wash buffers by simultaneous draining and filling of the flow device of the invention; (6) substrate is washed for a period of time; (7) the wash buffer is replaced with a subsequent wash buffer by simultaneous draining and filling of the flow device; and (8) following the last wash, the substrate is dried by a method suited to its hydrophobic or hydrophilic surface properties.

Certain embodiments of the present invention substantially reduce or eliminate cross-contamination inherent in batch processing. Batch processing of support substrates, through the required multiple wash process steps, is a common manual-methods practice. Batching increases the throughput and reduces the handling effort. It also exposes substrates to each other increasing the risk of cross-hybridization. Certain embodiments of the flow device of this invention reduce or eliminate the risk of exposing each substrate to contaminants from other substrates because they share the same wash-buffer bath. Each substrate is individually processed with fresh reagents at each process step.

Certain embodiments of the present devices are self-cleaning. Certain embodiments of the present invention incorporate the necessary fluidic architecture and controls to automatically clean up the fluid paths and flow-cells between uses. Additional valves and reagent reservoirs are provided for this purpose.

The design of certain embodiments of the present apparatus are modular and can be easily scaled. Certain embodiments of the present invention provide means to increase process throughput by expanding the capacity of the design to process more substrates simultaneously. Throughput can be increased by a factor of N by replicating the process flow device, associated pump and heat exchanger as well as subsets of valves and electronics controls N-times.

With certain embodiments of the present flow device, the substrate surface is completely irrigated. A moderate volume flow device completely encloses the microarray substrate during processing ensuring that all portions of the surface come in contact with the process fluids. Prior art that uses one or more O-rings to form limited control volumes against the active side of the substrate inherently wash only portions of the substrate during processing. The surface areas not washed are at risk of retaining waste residues that degrade the microarray image when scanned. Furthermore, the substrate surface regions near O-ring boundaries especially near interior corners are vulnerable to poor fluid circulation and subsequently experience ineffective cleansing.

In certain embodiments of the present invention, high-volume washing is more effective. Many automated hybridization stations form a small fluid control volume (order of about 300 microliters or less) over the active surface of the microarray substrate. This small volume is advantageous to the hybridization process steps since it reduces the amount of hybridization buffer and target material needed for effective hybridization. This small volume turns into a disadvantage at the point in the processing following incubation, when the microarray must be washed. This invention provides a large volume wash (about 20 mL to about 200 mL of fluid reagent per wash) with a large control volume. It offers higher instantaneous dilution ratios to improve the removal of non-specifically bound target, and the salts and detergents associated with the wash reagents.

Certain embodiments of the present invention provide fluid re-circulation. A common manual-methods practice is to wash substrates in open-top histology slide staining glassware. This glassware is placed on electric hot-plates, surrounded by ice-baths or left at room temperature as necessary, but in all cases the wash reagents are agitated to improve washing action. The common method uses hot plates or stir-plates incorporating magnetic stirrers and spin bars. This practice is effective. However, automated hybridization stations usually wash by flowing a small volume of wash reagent through the small control volume that covers the active side of the substrate, sometimes accompanied by microliter volume fluid agitation. Such techniques result in ineffective washing and the undesired retention of residues on the substrate surface. This invention provides vigorous agitation during washing by re-circulating the wash reagent through the flow device with the aid of a high-capacity pump. After the flow device has been filled with wash reagent, the fluid is simultaneously drained from the bottom of the flow device and re-injected at the top of the flow device. This flow-through action of the wash reagent results in a high level of agitation.

Wash reagents are temperature controlled in the present invention to maintain their stringencies. The wash protocols for processing microarray substrates specify particular salt concentrations and process temperatures that are unique to the substrate surface chemistry and the $T_m$ properties of the probe and target polynucleotide duplex. It is essential to maintain the stringency of the wash reagents during processing in order to obtain consistent hybridization results. Manual-method practices commonly use human-in-the-loop temperature control. When new reagent replaces spent reagent, time must be allowing for the new reagent to reach the correct process temperature. Throughout this process, when the human is occupied performing other activities, the temperatures may deviate from ideal. In most automated hybridization stations, provision is made to control the temperature of the wash reagents, but only at the time of use as they are applied to the substrate surface. Usually, automated hybridization stations only heat the reagents, not cool them.

In certain embodiments of this invention, multiple reagent reservoirs are provided to the user. Several of these are independently temperature controlled above room temperature (pre-heated) and one below room temperature (pre-cooled). Furthermore, this invention maintains the intended operating temperature of these reagents as they are re-circulated through the flow device during the wash process steps.

In certain embodiments of the present invention, fluids are moved by positive pressure and fluid pumping. Certain embodiments of the present invention use a combination of positive gas pressure and fluid pumping to move wash and cleaning reagents through the fluid circuits. Dry nitrogen or clean dry air above atmospheric pressure pressurizes the reagent reservoirs. A positive-displacement pump moves fluids between sources and destinations. This dual method is an improvement over automated hybridization stations that commonly use only vacuum (negative gas pressure) to move fluids. To further improve performance, fluid transfers are not controlled by or dependent on pumping times or gas pressures. Such control methods lead to inaccurate filling and draining. In this invention, fluid level sensors are placed at key points in the fluidic design to detect fluid levels such as a full or empty flow device, empty reagent reservoirs, full waste reservoir, etc.

Certain embodiments of the present invention provide for near-vertical substrate slow-drain drying. Certain embodiments of the present invention improve upon known manual and automated methods. Certain embodiments of the present invention position the microarray substrate in a near vertical orientation within the process flow-cell. Substrate drying is achieved by controlled pump-out (slow-draining) of the final wash reagent. Drying is achieved without the need to remove the substrate, or apply a pressurized gas stream to the substrate or spin the substrate in a centrifuge-like device. During pump-out, the rectangular substrate may be oriented with one corner lower than all the others to facilitate the collection of all fluid droplets at one final place on the body of the substrate. In this manner fluid is completely removed from all six faces of the microarray substrate, an improvement over the prior art. An equivalent alternative to the slow-drain method described immediately above, is to slowly lift the substrate from the final wash pool. If the withdrawal rate is equal to the pump-out rate in terms of the velocity of the air-fluid interface, then equivalent drying performance may be achieved. The controlled pump-out or the slow-lift as just described provides effective drying of hydrophobic substrate surfaces. Its effectiveness, in drying hydrophilic substrate surfaces, is significantly enhanced when a solvent vapor gently fills the gas space displaced by the pumped-out fluid at the air-fluid interface.

In some embodiments of the present invention, solvent vapor assists drying of hydrophilic substrate surfaces. Some microarray substrates have hydrophilic surfaces as explained above. Such surfaces may be dried more efficiently in accordance with the present invention by favorably altering surface tension, creating a surface tension gradient in the meniscus, thus 'encouraging' the fluid to flow off the substrate and into the reagent pool. The method to achieve such a gradient flow is to make present a low-concentration of solvent vapor at the gas-fluid interface. This alters the surface tension of the fluid film attached to the hydrophilic surface and causes it to flow toward the fluid pool leaving the receding hydrophilic surface dry. Certain embodiments of the present invention provide a solvent reservoir and the associated pneumatic circuitry and controls to inject a solvent vapor into the flow device during the slow-drain drying process step for hydrophilic substrates. This solvent vapor enhances the drying process. When the flow device is completely drained of wash reagent, the solvent vapor is purged and replaced by inert dry nitrogen gas at atmospheric pressure.

EXAMPLE

The invention is demonstrated further by the following illustrative example. The objective of this example is to automatically wash and dry microarray substrates involved in hybridization reactions in a consistent and reproducible manner. Subsequent to the hybridization reactions, the microarray substrates are subjected to a sequence of multiple wet and dry processes to achieve the removal of undesired hybridization fluids, target polynucleotide material, wash residues and related solid and liquid waste products.

The following protocols are followed depending on the manner in which the microarray substrate is prepared (in situ synthesis, or whole oligonucleotide or cDNA deposition).

| Protocol Step | in situ Synthesized | Whole Oligo and cDNA Deposition |
| --- | --- | --- |
| Disassembly Wash | Disassemble quickly in 60° C. 6X SSC + 0.005% TX-102. | Disassemble quickly in room temperature 0.5X SSC + 0.01% SDS. |
| Wash #1 | Wash for 10 minutes in room temperature 6X SSC + 0.005% TX-102 with agitation. | Wash for 5 minutes in room temperature 0.5X SSC + 0.01% SDS with agitation. |
| Wash #2 | Wash for 5 minutes in 4° C. 0.1X SSC + 0.005% TX-102 with agitation. | Wash for 2 minutes in room temperature 0.06X SSC with agitation. |
| Dry | Nitrogen gas blow-dry. | Centrifuge spin-dry at 1200 RPM for 2 minutes. |

The aforementioned protocols are carried out using an apparatus and flow devices as described above and illustrated in the accompanying figures. Four wash reagents are employed, each in an independent wash reagent reservoir that is part of the apparatus used. The apparatus is controlled by a microprocessor, which has all necessary control buttons for operation of the apparatus. The procedures for operating the apparatus and the general process flow for washing and drying substrates is outlined in the following text wherein the term:

'Human: . . . ' designates human operator action and the term: 'Machine: . . . ' designates machine action.

Human:

1. Initiate machine activity by pressing the 'start' control button.

Machine:

2. Close all valves (304, 324, 348, 360, 362, 365, 366, 368, 378). Set valve 312 to re-circulate. Stop pump 310.
3. Pre-heat disassembly reagent (376) and wash reagent #1 (322) as required by protocols.
4. Pre-cool wash reagent #2 (302) as required by protocols.
5. Lower the substrate magnetic lifter to the bottom of the flow-cell (apparatus 338, 339, 340, 342, 344)
6. Wait until the reagents reach their set-point temperatures. When this is achieved, indicate 'ready' status.
7. Select flow-cell number.
8. Select which wash & dry protocol to run for the selected flow-cell.

Machine:

9. Open valves 378 & 366 to fill selected flow-cell (300) with disassembly reagent (376).
10. Close valves 378 & 366. Set valve 312 to re-circulate and activate pump 310 to re-circulate flow-cell reagent and maintain it at the temperature using heat exchanger 316 as required by protocol.

Human:

11. Remove hybridization chamber from incubator.
12. Manually disassemble the hybridization chamber to extract microarray substrate or sandwich.
13. Place microarray substrate or sandwich into selected flow-cell and allow it to submerge.
14. Initiate machine action by pressing the 'disassemble & wash' control button.

Machine:

15. Indicate 'busy' status.
16. Set valve 312 to re-circulate and operate pump 310 to re-circulate disassembly reagent, in selected flow-cell (300), to rinse the substrate.
17. Maintain the flow-cell reagent temperature via heat exchanger 316 and re-circulate the fluid for the period of time specified by protocol (usually 10 seconds or less), then . . . .
18. Open valves 324 & 366. Set valve 312 to drain and operate pump 310 to replace the disassembly reagent in chamber 300 with wash reagent #1 (322), in the selected flow-cell by draining the spent reagent while simultaneously filling the flow-cell with fresh wash reagent #1.
19. Indicate 'first-wash busy' status.
20. Close valves 324 & 366. Set valve 312 to re-circulate and operate pump 310 to re-circulate wash reagent #1, in selected flow-cell, to wash the substrate.
21. Maintain the flow-cell reagent temperature using heat exchanger 316 and re-circulate the fluid for the period of time specified by protocol (10 minutes for Agilent's in situ microarrays and 5 minutes for Agilent's cDNA and Whole Oligo microarrays), then
22. Open valves 304 & 366. Set valve 312 to drain and operate pump 310 to replace the wash reagent #1 with wash reagent #2 (302), in the selected flow-cell by draining the spent reagent while simultaneously filling the flow-cell with fresh wash reagent #2.
23. Indicate 'second-wash busy' status.
24. Close valves 304 & 366. Set valve 312 to re-circulate and operate pump 310 to re-circulate wash reagent #2, in selected flow-cell, to wash the substrate.
25. Maintain the flow-cell reagent temperature using heat exchanger 316 and re-circulate the fluid for the period of time specified by protocol (5 minutes for Agilent's in situ microarrays and 2 minutes for Agilent's cDNA and Whole Oligo microarrays), then . . . .

If the microarray substrate has a hydrophilic surface then proceed with steps 26-33 otherwise proceed with steps 34-40.

26. Indicate 'drying busy' status.
27. Tip flow-cell toward the horizontal approximately 18 degrees (for a 1 inch×3 inch slide) to orient the substrate for best draining with apparatus 336.
28. Open valves 348 & 362. Set valve 312 to drain and operate pump 310 to drain flow-cell fluid by controlled pump-out while simultaneously injecting low-pressure solvent vapor from supply 346.
29. Pump-out until empty sensor (334) indicates no fluid remains.
30. Return the flow-cell to its normal vertical orientation.
31. Close valve 348 and open valve 365 to purge flow-cell containing organic solvent vapor with air (or nitrogen gas) for 10 seconds, then vent flow-cell to ambient atmosphere by closing valve 365 and opening valve 360.
32. Raise the microarray substrate elevator to eject the substrate from flow-cell using lift apparatus 338, 339, 340, 342, 344
33. Indicate 'done' status If the microarray substrate has a hydrophobic surface then proceed as follows:

34. Indicate 'drying busy' status.
35. Tip flow-cell toward the horizontal approximately 18 degrees (for a 1 inch×3 inch slide) to orient the substrate for best draining with apparatus 336.
36. Open valves 360 & 362. Set valve 312 to drain and operate pump 310 to drain flow-cell fluid by controlled pump-out until empty sensor (334) indicates no fluid remains.
37. Return the flow-cell to its normal vertical upright orientation.
38. Leave valve 360 open to vent flow-cell (300) to ambient atmosphere.
39. Raise the microarray substrate elevator to eject substrate from flow-cell using lift apparatus 338, 339, 340, 342, 344.
340. Indicate 'done' status.

After the apparatus if finished being used to wash and dry substrates it can be cleaned by the following process.

Human:

41. Initiate machine action by pressing the 'clean-up' control button

Machine:

42. Indicate 'cleaning' status.
43. Open valve 360 & 362 to vent flow-cell to ambient atmosphere.
44. Set valve 312 to drain and operate pump 310 to drain flow-cell fluid by controlled pump-out until empty sensor (334) indicates no fluid remains.
45. Open valves 368 & 366. Fill selected flow-cell (300) with cleaning reagent (370) until full sensor (332) indicates full.
46. Close valves 368 & 366. Set valve 312 to re-circulate and operate pump 310 to re-circulate cleaning reagentfor ~10 seconds, in selected flow-cell, to rinse fluid surfaces.
47. Set valve 312 to drain and operate pump 310 to drain flow-cell fluid by controlled pump-out until empty sensor (334) indicates no fluid remains.

48. Repeat the fill, re-circulate & drain steps (45-47 above) as many times as necessary to clean apparatus, then, close all valves and stop pump 310.
49. Indicate 'done' status.

It should be understood that the above description is intended to illustrate and not limit the scope of the invention. Other aspects, advantages and modifications within the scope of the invention will be apparent to those skilled in the art to which the invention pertains. The following examples are put forth so as to provide those of ordinary skill in the art with examples of how to make and use the method and products of the invention, and are not intended to limit the scope of what the inventors regard as their invention.

All publications and patent applications cited in this specification are herein incorporated by reference as if each individual publication or patent application were specifically and individually indicated to be incorporated by reference, except insofar as they may conflict with those of the present application (in which case the present application prevails). Methods recited herein may be carried out in any order of the recited events that is logically possible, as well as the recited order of events.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A device for conducting processing steps on a substrate comprising an array of chemical compounds on a surface thereof, said device comprising:
    (a) a housing comprising a housing chamber configured to retain any fluid introduced into said housing chamber, said fluid having a meniscus,
    (b) an opening in said housing adapted for insertion into said housing chamber of a substrate having a surface comprising an array of chemical compounds,
    (c) a fluid separation mechanism configured to separate fluid in said housing chamber from contact with said substrate in a controlled manner that preserves the integrity of the fluid meniscus at the atmosphere-fluid interface, wherein said fluid separation mechanism is a fluid removal mechanism for removing fluid from said housing chamber in said controlled manner, said fluid removal mechanism comprising a valve having a varying cross-section relative to height of fluid in said housing chamber,
    (d) at least one inlet in fluid communication with said housing chamber, and (e) at least one outlet in fluid communication with said housing chamber.

2. A device according to claim 1 further comprising a tilt mechanism for controlling the orientation of said device.

3. A device according to claim 1 wherein said fluid removal mechanism comprises a valve or a pump.

4. A device according to claim 1 wherein said fluid removal mechanism comprises a pump having a constant displacement.

5. A device according to claim 1 further comprising a temperature controller.

6. A device according to claim 1 further comprising a means for cooling a fluid.

7. A device according to claim 1 further comprising a heat exchanger for heating and/or cooling a fluid.

8. A device according to claim 1 further comprising a solvent vapor generator.

9. The device of claim 1 further comprising a wedge positioned to insert between and separate a sandwich of said substrate and a cover slide positioned in said housing chamber to expose said surface of said substrate to fluid within said housing chamber.

10. A device according to claim 9 further comprising a pair of flexible members adjacent said wedge.

11. A flow device comprising:
    (a) a reaction chamber having an opening for insertion of a substrate into said reaction chamber, said substrate having a cover slide over a surface thereof wherein said surface comprises a plurality of biopolymers, and
    (b) a separator mechanism for separating said substrate surface from said cover slide while in said reaction chamber without damage to said biopolymers on said surface, said separator mechanism comprising a pair of flexible members having a wedge member therebetween disposed to insert between and separate said substrate surface from said cover slide.

12. The flow device of claim 11, wherein said separator mechanism is configured to separate said substrate from said cover slide to expose said plurality of biopolymers to fluid within said housing chamber.

13. The flow device of claim 11, wherein said wedge member is positioned to separate said substrate from said cover slide to expose said plurality of biopolymers to fluid within said housing chamber.

14. The flow device of claim 11, wherein said separator mechanism is configured to part said substrate from said cover slide to expose said plurality of biopolymers to fluid within said housing chamber.

15. The flow device of claim 11, wherein said wedge member is positioned to part said substrate from said cover slide to expose said plurality of biopolymers to fluid within said housing chamber.

* * * * *